US011492370B2

(12) United States Patent
Hoveyda et al.

(10) Patent No.: US 11,492,370 B2
(45) Date of Patent: Nov. 8, 2022

(54) METHOD OF MAKING A CROSS METATHESIS PRODUCT

(71) Applicant: Trustees of Boston College, Chestnut Hill, MA (US)

(72) Inventors: Amir H. Hoveyda, Lincoln, MA (US); Chaofan Xu, Newton, MA (US); Xiao Shen, Waltham, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 353 days.

(21) Appl. No.: 16/626,234

(22) PCT Filed: Jul. 20, 2018

(86) PCT No.: PCT/US2018/043106
§ 371 (c)(1),
(2) Date: Dec. 23, 2019

(87) PCT Pub. No.: WO2019/018773
PCT Pub. Date: Jan. 24, 2019

(65) Prior Publication Data
US 2020/0123197 A1     Apr. 23, 2020

Related U.S. Application Data

(60) Provisional application No. 62/535,117, filed on Jul. 20, 2017.

(51) Int. Cl.
*B01J 31/00* (2006.01)
*C07K 1/107* (2006.01)
*B01J 31/22* (2006.01)
*C07C 51/353* (2006.01)
*C07D 313/00* (2006.01)

(52) U.S. Cl.
CPC ........... *C07K 1/107* (2013.01); *B01J 31/2295* (2013.01); *C07C 51/353* (2013.01); *C07D 313/00* (2013.01)

(58) Field of Classification Search
None
See application file for complete search history.

(56) References Cited

U.S. PATENT DOCUMENTS 6,215,019 B1    4/2001 Pederson et al.

FOREIGN PATENT DOCUMENTS

| DE | 102009017498 A1 | 10/2010 |
|---|---|---|
| WO | 200172421 | 10/2001 |
| WO | 2006138166 | 12/2006 |
| WO | 2014201300 | 12/2014 |

OTHER PUBLICATIONS

International Search Report and Written Opinion dated Nov. 5, 2018 for international application PCT/US2018/043106.
Grandbois, et al., "Enantioselective Synthesis of [7]Helicene: Dramatic Effects of Olefin Additives and Aromatic Solvents in Asymmetric olefin Metathesis", Chemistry—A European Journal, 2008, vol. 14, No. 30, pp. 9323-9329.
Hong, et al., "Prevention of Undesireable Isomerization During Olefin Metathesis", Journal of the American Chemical Society, 2005, vol. 127, No. 49, pp. 17160-17161.
Kotha, et al., "Recent Applications of Ring-Rearrangement Metathesis in Organic Synthesis", Beilstein Journal of Organic Chemistry, 2015, vol. 11, pp. 1833-1864.
Xu, et al., "In Situ Methylene Capping: A General Strategy for Efficient Implications and applications to Synthesis of Biologically Active Compounds", Journal of the American Chemical Society, 2017 [E-Pub.: Jul. 27, 2017], vol. 139, No. 31, pp. 10919-10928.
Xu, et al., "Synthesis of Z-or E-Trisubstituted Allylic Alcohols and Ethers by Kinetically Controlled Cross-Meathesis with a Ru Catechothiolate Complex", Journal of the American Chemical Society, 2017 [E-Pub.: Oct. 25, 2017], vol. 139, No. 44. pp. 15649-15643.
Yoshida, et al., "Ring Size-Selective Ring-Closing Olefin Metathesis: Taking Advantage of the Deleterious Effect of Ethylene Gas", Advanced Synthesis & Catalysis, 2011, vol. 353, No. 8, pp. 1229-1233.
Extended European Search Report dated Mar. 18, 2021 for EP Application 18835122.5.
Lysenko, et al., "Stability of the first-generation Grubbs metathesis catalyst in a continuous flow reactor", Journal of Organometallic Chemistry, Elsevier, Amsterdam, NL, vol. 691, No. 24-25, Dec. 1, 2006 (Dec. 1, 2006), pp. 5197-5203, XP028048251.
Ulman, et al., "Ruthenium Carbene-Based Olefin Metathesis Initiators: Catalyst Decomposition and Longevity", Journal of Organic Chemistry, American Chemical Society, Washington, vol. 64, No. 19, Sep. 17, 1999 (Sep. 17, 1999) pp. 7202-7207, XP001037574.
Third Party Observations dated Jun. 2, 2022 for EP 20180835122.

*Primary Examiner* — Jeanette M Lieb
(74) *Attorney, Agent, or Firm* — Dorsey & Whitney LLP

(57) ABSTRACT

Method of making a cross metathesis product, the method comprising at least step (X) or step (Y): (X) reacting in a cross metathesis reaction a first compound comprising a terminal olefinic group with a second compound comprising a terminal olefinic group, wherein the first and the second compound may be identical or may be different from one another; or (Y) reacting in a ring-closing metathesis reaction two terminal olefinic groups which are comprised in a third compound; wherein the reacting in step (X) or step (Y) is performed in the presence of a ruthenium carbene complex comprising a [Ru=C]-moiety and an internal olefin.

33 Claims, No Drawings

METHOD OF MAKING A CROSS METATHESIS PRODUCT

CROSS-REFERENCE TO RELATED APPLICATIONS

This patent application is the U.S. National Stage filing under 35 U.S.C. 371 of International Patent Application No. PCT/US2018/043106 entitled "METHOD OF MAKING A CROSS METATHESIS PRODUCT," filed Jul. 20, 2018, which claims priority to U.S. Provisional Patent Application No. 62/535,117, entitled "METHOD OF MAKING A CROSS METATHESIS PRODUCT," filed Jul. 20, 2017, each of which is incorporated herein by reference in its entirety.

STATEMENT REGARDING FEDERALLY SPONSORED RESEARCH OR DEVELOPMENT

This invention was made with government support under Grant No. CHE-1362763 awarded by the National Science Foundation. The government has certain rights in the invention.

FIELD OF THE INVENTION

The invention relates to a method of making a cross metathesis product from two terminal olefins or from two terminal olefinic groups which are comprised in one compound using a Ru carbene complex comprising a [Ru=C]-moiety such as a [Ru alkylidene]-moiety. The invention further relates to a method of reducing activity loss of a Ru carbene complex comprising a [Ru=C]-moiety when using said complex in a metathesis reaction in which ethylene is developed.

BACKGROUND OF THE INVENTION

It is known that of all ruthenium carbene complexes comprising a [Ru=C]— moiety such as a [Ru alkylidene]-moiety decomposition of the ruthenium methylidene is most significant. This ruthenium methylidene is significant since it is the propagating species in alkene metathesis involving 1-alkenes (α-olefins, terminal olefins) due to the formation of ethylene. The ruthenium methylidene species (Ru=$CH_2$ species) may be formed in metathesis reactions with e.g. a Grubbs catalyst. The ruthenium methylidene decomposes thermally, e.g. when heated in benzene at a temperature of 55° C. to produce a dinuclear ruthenium hydride. This decomposition temperature is comparable to that used in routine cross metathesis reactions. Accordingly, cross metathesis reactions in which ruthenium methylidene complexes are generated are hampered due to thermal decomposition of the complex resulting in activity loss towards metathesis. The main reaction is then alkene isomerization caused by the dinuclear complex rather than metathesis. Said unwanted isomerization was suppressed by using benzoquinone as an additive in case of metathesis of allylic ethers and long-chain aliphatic alkenes (Hong, S. H., Sanders, D. P., Lee, C. W., Grubbs, R. H., J. Am. Chem. Soc. 2005, 127, 17160-17161).

It is further known that catalysts with high stability may usually suffer from poor reactivity in metathesis reactions. This will need to be balanced with increased metathesis reactivity. This is of particular relevance in industrial applications.

Objects of the Invention

Due to the ongoing need for high turnover catalysts in industrial applications, i.e. catalysts being active without losing reactivity, one object of the invention was to provide a method for providing cross metathesis products made from compounds having one or more terminal olefinic groups using ruthenium catalysts comprising a Ru carbene moiety [Ru=C] while suppressing or avoiding the formation of undesired ruthenium methylidene complexes as far as possible.

SUMMARY OF THE INVENTION

This object was achieved with a method of making a cross metathesis product as defined in the following items 1 to 31 and a method of reducing activity loss of a Ru carbene complex comprising a [Ru=C]-moiety as defined in items 32 and 33:

1. Method of making a cross metathesis product, the method comprising at least step (X) or step (Y):
   (X) reacting in a cross metathesis reaction a first compound comprising a terminal olefinic group with a second compound comprising a terminal olefinic group, wherein the first and the second compound may be identical or may be different from one another; or
   (Y) reacting in a ring-closing metathesis reaction two terminal olefinic groups which are comprised in a third compound;
   wherein the reacting in step (X) or step (Y) is performed in the presence of a ruthenium carbene complex comprising a [Ru=C]-moiety and in the presence of an internal olefin which may be a Z-olefin or an E-olefin.
2. Method of item 1, wherein more than 1 equivalent of said internal olefin is used per equivalent of said first or second compound, respectively said third compound.
3. Method of item 1 or 2, further comprising step (Z) after step (X) or step (Y):
   (Z) removing said internal olefin and/or a metathesis product which is formed from said internal olefin in step (X) or step (Y).
4. Method of any one of the preceding items, wherein said internal olefin is a $C_{4-8}$ olefin.
5. Method of any one of the preceding items, wherein said internal olefin is Z-2-butene or E-2-butene.
6. Method of any one of the preceding items, wherein the first, the second or the third compound comprise one or more functional groups, respectively.
7. Method of any one of the preceding items, wherein the first and the second compound are independently from one another an alcohol, an ether, a carboxylic acid, an ester, an aldehyde, a ketone, a halogen containing compound, an amine, an amide, an imide, a sulfone, a sulfonic acid, an ester of a sulfonic acid, an internal olefin or an alkyne; or wherein the third compound is an alcohol, an ether, a carboxylic acid, an ester, an aldehyde, a ketone, a halogen containing compound, an amine, an amide, an imide, a sulfone, a sulfonic acid, an ester of a sulfonic acid, an internal olefin or an alkyne.
8. Method of any one of the preceding items, wherein the first and the second compound used in step (X) comprise independently an amino acid moiety or a peptide moiety.
9. Method of any one of items 1 to 7, wherein the third compound used in step (Y) comprises a peptide moiety.
10. Method of item 9, wherein the third compound used in step (Y) is of formula (B)

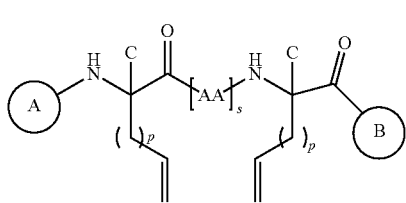

(B)

wherein

AA is any amino acid moiety;

A is independently hydrogen, a functional group, a protecting group, an optionally substituted amino acid residue, an optionally substituted peptide residue, a solid support, or any combination thereof;

B is independently hydrogen, a functional group, a protecting group, an optionally substituted amino acid residue, an optionally substituted peptide residue, a solid support, or any combination thereof;

C is independently H, $C_1$-$C_4$ alkyl, phenyl;

p is independently 1-4; and s is independently 1-10.

11. Method of item 10, wherein the peptide formed by ring-closing metathesis of the compound of formula (B) is a stapled peptide.

12. Method of any one of the preceding items, wherein said ruthenium carbene complex comprising a [Ru=C]-moiety is of formula I:

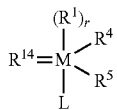

I wherein:

M is ruthenium;

each of $R^1$ and L is independently a neutral ligand;

r is 1-3;

each of $R^4$ and $R^5$ is independently bonded to M through a sulfur or oxygen atom;

$R^{14}$ is a carbene;

$R^4$ and $R^5$ are taken together to form a bidentate ligand, or $R^4$ and $R^5$ are taken together with one or more of $R^1$, L and $R^{14}$ to form a polydentate ligand;

two or more of $R^1$, L and $R^{14}$ are optionally taken together to form a bidentate or polydentate ligand; and each of $R^1$, $R^4$, $R^5$, L and $R^{14}$ is independently and optionally linked to a tag or support.

13. Method of item 12, wherein $R^4$ and $R^5$ form a dithiolate, preferably a catechodithiolate.

14. Method of item 12 or 13, wherein said carbene $R^{14}$ is a benzylidene, preferably which is at least substituted in the phenyl ring in ortho position with a $C_1$-$C_4$ alkoxy group.

15. Method of any one of items 12 to 14, wherein $R^1$ is a nitrogen-containing heterocyclic carbene and r=1.

16. Method of any one of items 1 to 11, wherein the complex is of formula 4 or formula 5

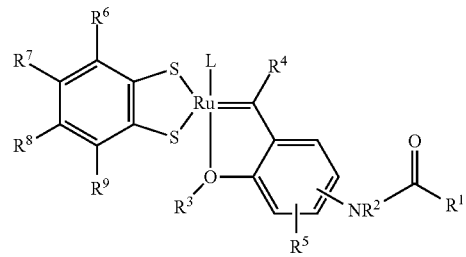

4

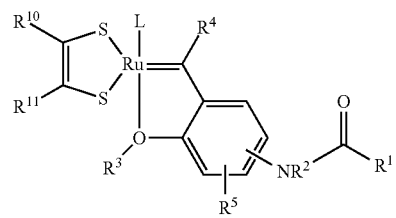

5 wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:

L is: a neutral ligand;

$R^1$ is: H;
  unbranched or branched $C_{1-20}$ alkyl or unbranched or branched $C_{1-20}$ alkoxy; $C_{5-9}$ cycloalkyl or $C_{5-9}$ cycloalkoxy; optionally bearing one or more halogen atoms, respectively; or
  aryl or aryloxy; optionally substituted, respectively, with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;

$R^2$ is: H; unbranched or branched $C_{1-20}$ alkyl; aryl; —C(O)$R^{12}$; —C(O)O$R^{12}$; —C(O)C(O)$R^{12}$; —C(O)C(O)O$R^{12}$; wherein $R^{12}$ has the meaning of $C_{1-20}$ alkyl or aryl, respectively; $R^{12}$ optionally bearing one or more halogen atoms;

$R^3$ is: unbranched or branched $C_{1-20}$ alkyl; aryl; or
  $R^{13}$—C(O)—CHR$^{14}$, wherein $R^{13}$ is $C_{1-20}$ alkoxy and $R^{14}$ is H or $C_{1-20}$ alkyl; or wherein $R^{13}$ is $C_{1-20}$ alkoxy and $R^{14}$ is C(O)—O—$C_1$20 alkyl; or wherein $R^{13}$ is $C_{1-20}$ alkyl and $R^{14}$ is H; or $R^{13}$ is OH and $R^{14}$ is H or $C_{1-20}$ alkyl; or
  $R^{15}$—O—N($R^{16}$)—C(O)—CHR$^{17}$, wherein $R^{15}$, $R^{16}$, and $R^{17}$ are independently H or $C_{1-20}$ alkyl;

$R^4$ is: H;

$R^5$, $R^6$, $R^7$, $R^8$, $R^9$, $R^{10}$ and $R^{11}$ are, independently, H; unbranched or branched $C_{1-20}$ alkyl or unbranched or branched $C_{1-20}$ alkoxy; $C_{5-9}$ cycloalkyl or $C_{5-9}$ cycloalkoxy; aryl; aryloxy; unbranched or branched $C_{1-20}$ alkylcarbonyl; arylcarbonyl; unbranched or branched $C_{1-20}$ alkoxycarbonyl; aryloxycarbonyl; heteroaryl; carboxyl; cyano; nitro; amido; aminosulfonyl; N-heteroarylsulfonyl; unbranched or branched $C_{1-20}$ alkylsulfonyl; arylsulfonyl; unbranched or branched $C_{1-20}$ alkylsulfinyl; arylsulfinyl; unbranched or branched $C_{1-20}$ alkylthio; arylthio; sulfonamide; halogen; or $N(R^y)(R^z)$, wherein $R^y$ and $R^z$ are independently selected from H and $C_{1-20}$ alkyl; or aryl or aryloxy, respectively substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

17. Method of item 16, wherein in formula 4 or 5 the neutral ligand L is $P(R^x)_3$, wherein $R^x$ is independently branched or unbranched $C_{1-20}$ alkyl or $C_{1-20}$ alkoxy, $C_{5-9}$ cycloalkyl, or aryl; or RCN, wherein R is branched or unbranched $C_{1-20}$ alkyl, $C_{5-9}$ cycloalkyl, or aryl; or a carbene containing the moiety of formula 6

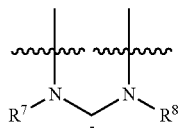

6 wherein $R^7$ and $R^8$ as defined in formula 6 are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen.

18. Method of item 16 or 17, wherein L in formula 4 or 5 is a carbene of one of formulas 6a, 6b, 6c or 6d:

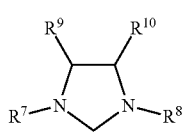

6a

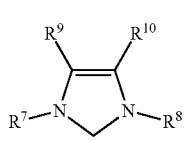

6b

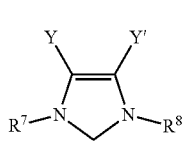

6c

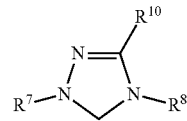

6d wherein $R^9$ and $R^{10}$ are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$ alkoxy or halogen; or $R^9$ and $R^{10}$ together with the carbon atoms to which they are attached are combined to form a carbocyclic 3 to 8 membered ring;

Y and Y' are halogen.

19. Method of any one of items 16 to 18, wherein $R^1$ is $C_{1-6}$ alkyl, optionally substituted with one or more of halogen; or phenyl, optionally substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

20. Method of any one of items 16 to 19, wherein $R^2$ is H.

21. Method of any one of items 16 to 20, wherein $NR^2$—$C(O)$—$R^1$ is in para-position with respect to O.

22. Method of any one of items 16 to 21, wherein $R^3$ is methyl or isopropyl.

23. Method of any one of items 16 to 22, wherein $R^5$ is H.

24. Method of any one of items 16 to 23, wherein $R^6$, $R^7$, $R^8$, and $R^9$ in formula 4 are independently selected from H and halogen.

25. Method of any one of items 16 to 24, wherein $R^{10}$ and $R^{11}$ as defined in formula 5 are independently selected from halogen and cyano.

26. Method of any one of items 16 to 25, wherein L is of formula 6a or 6b, preferably wherein $R^9$ and $R^{10}$ as defined in formula 6a or 6b are H, respectively, and $R^7$ and $R^8$ as defined in formula 6a and 6b are mesityl, or 2,6-diisopropylphenyl; or wherein L is of formula

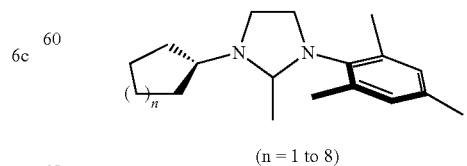

(n = 1 to 8)

27. Method of any one of items 16 to 26, wherein the complex is immobilized on a solid support.

28. Method of item 15 or 16, wherein $R^1$ as defined in item 15 or L as defined in claim 16 is a nitrogen-containing heterocyclic carbene of structure 7

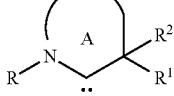

7 wherein the A-ring is a 4-, 5-, 6-, or 7-membered ring; and L in formula 7 is a linking group representing from one to four ring vertices selected from carbon with available valences optionally occupied by hydrogen or optionally substituted by $C_{1-10}$ alkyl and aryl, optionally substituted;

R in formula 7 represents a member selected from $C_{1-10}$ alkyl and aryl, optionally substituted;

$R^1$ and $R^2$ in formula 7 represent independently members selected from $C_{1-10}$ alkyl and aryl, optionally substituted.

29. Method of item 28, wherein the nitrogen-containing carbene is of formula 7a or 7b:

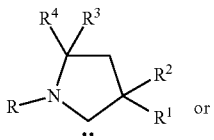

7a

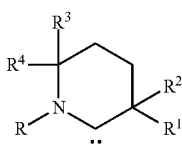

7b wherein R, $R^1$, $R^2$, $R^3$ and $R^4$ in formulae 7a and 7b independently represent a member selected from $C_{1-10}$ alkyl and aryl, optionally substituted.

30. Method of any one of items 1 to 11, wherein the complex is selected from one of the following structures:

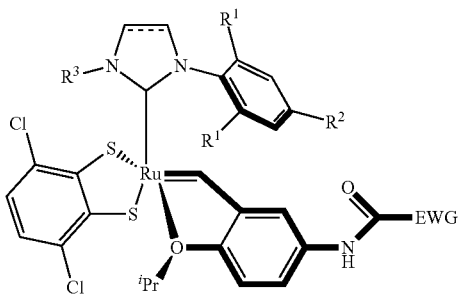

-continued

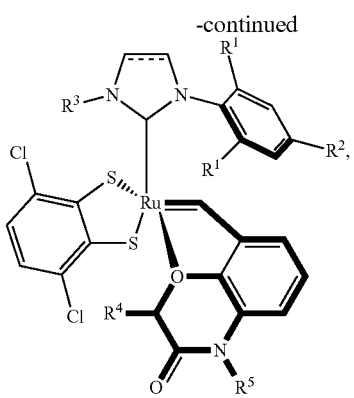

wherein
$R^1$ = Me, $^i$Pr. $R^2$ = Me, H. $R^3$ = Ar, Cycloalkyl,
$R^4$ = Alkyl. $R^5$ = H, C(O)EWG and EWG is an electron-withdrawing group.

31. Method of any one of the preceding items, wherein more than 50% or 60% or 70% or 80% of the olefin formed in the metathesis reaction according to step (X) or step (Y) is a Z-olefin, provided said internal olefin is a Z-olefin, preferably Z-2-butene; or wherein the olefin formed in the metathesis reaction according to step (X) is generated predominantly as E-olefin, provided said internal olefin is an E-olefin, preferably E-2-butene; or wherein the olefin formed in the metathesis reaction according to step (Y) is generated predominantly as E-olefin, provided said internal olefin is an E-olefin, preferably E-2-butene, and the ring-closing metathesis reaction allows the formation of an E-olefin depending on the ring size.

32. Method of reducing activity loss of a Ru carbene complex comprising a [Ru=C]-moiety when using said complex in a metathesis reaction in which ethylene is developed, the method comprising step (V):

(V) performing said reaction in the presence of an internal olefin which may be a Z-olefin or an E-olefin.

33. Method of item 32, wherein said internal olefin is Z-2-butene or E-2-butene.

DETAILED DESCRIPTION OF THE INVENTION

In the following, all terms in quotation marks are defined in the meaning of the invention.

In a first aspect, the invention relates to a method of making a cross metathesis product, the method comprising at least step (X):

(X) reacting in a cross metathesis reaction a first compound comprising a terminal olefinic group with a second compound comprising a terminal olefinic group, wherein the first and the second compound may be identical or may be different from one another;

wherein the reacting in step (X) is performed in the presence of a ruthenium carbene complex comprising a [Ru=C]-moiety and an internal olefin.

In a second aspect, the invention relates to a method of making a cross metathesis product, the method comprising at least step (Y):

(Y) reacting in a ring-closing metathesis reaction two terminal olefinic groups which are comprised in a third compound;

wherein the reacting in step (Y) is performed in the presence of a ruthenium carbene complex comprising a [Ru=C]-moiety and an internal olefin.

Internal Olefin and Effect of the Invention Caused by Said Internal Olefin

It has been surprisingly found that the presence of an internal olefin in the method according to steps (X) and (Y) effectively promotes the cross metathesis reaction, respectively the ring-closing metathesis reaction, compared to reactions which are carried out in the absence of said internal olefin.

Without being bound by theory, the effect may be explained such that said internal olefin reacts under the influence of the Ru carbene catalyst with a terminal olefinic group faster than said two olefinic groups of the first and the second compound, respectively the third compound, with one another. Subsequently, the formed cross metathesis product of the internal olefin with a terminal olefinic group reacts with another terminal olefinic group. Accordingly, the formation of ethylene is reduced or even avoided that might lead to the formation of undesired Ru methylidene complexes.

However, even if a Ru methylidene complex is used as the catalyzing complex, it is conceivable that said internal olefin transforms said methylidene complex in a Ru carbene complex which is different from methylidene. Such formed complex is more stable than said methylidene complex and promotes metathesis.

Accordingly, in a preferred embodiment, the ruthenium carbene complex used in step (X) or step (Y) is not a ruthenium methylidene complex.

In another embodiment, the ruthenium alkylidene complex used in step (X) or step (Y) is a ruthenium methylidene complex.

In one embodiment, in order to push the balance to the side of a ruthenium carbene complex which is different from a ruthenium methylidene complex, preferably an excess of said internal olefin is used relative to the first compound or the second compound or the sum of the first and the second compound, respectively relative to the third compound.

In one embodiment, more than 1 equivalent of said internal olefin per equivalent of said first or second compound, respectively per equivalent of said third compound is used in step (X) or step (Y). Preferably, more than 2 or 3 or 5 or 10 or 20 equivalents of said internal olefin are used.

In another embodiment, from 3 to 30 equivalents, preferably from 5 to 20 equivalents of said internal olefin are used per equivalent of said first or second compound, respectively said third compound.

In one embodiment, it is advantageous if said excess of said third compound or a metathesis product produced from said internal olefin is removed subsequently to step (X) or step (Y). Metathesis products formed from said internal olefin are e.g. metathesis products with ethylene or the first, the second or the third compound.

Preferably, said excess or said metathesis products may be removed by distillation, preferably by distillation in vacuo.

Accordingly, in one embodiment, the method further comprises step (Z) after step (X) or step (Y):

(Z) removing said internal olefin or a metathesis product which is formed from said internal olefin in step (X) or step (Y), or removing said internal olefin and a metathesis product which is formed from said internal olefin in step (X) or step (Y).

In a preferred embodiment, said internal olefin is a $C_4$-$C_8$ olefin. In particular such $C_4$-$C_8$ olefins allow for a fast reactivity of said internal olefin with said first or second or third compound under metathesis conditions.

The term "$C_4$-$C_8$ olefin" encompasses straight as well as branched olefins.

In one embodiment, said internal olefin is a Z-olefin.

In another embodiment, said internal olefin is an E-olefin.

In a particularly preferred embodiment, said internal olefin is Z-2-butene.

In another preferred embodiment, said internal olefin is E-2-butene.

It has been discovered that the method according to the invention is highly Z-selective, i.e. that the olefins formed in step (X) or step (Y) are generated predominantly as Z-olefins, provided said internal olefin is a Z-olefin, preferably Z-2-butene.

The term "highly Z-selective" means that more than 50% of the formed cross metathesis products are Z-olefins.

In one embodiment, more than 60% or more than 70% or even more than 80% or 90% or 95% of the formed cross metathesis products are Z-olefins.

It has further been discovered that the method according to the invention is E-selective, i.e. that the olefins formed in step (X) or step (Y) are generated predominantly as E-olefins, provided said internal olefin is an E-olefin, preferably E-2-butene. Furthermore, the ring-closing metathesis reaction according to step (Y) must allow the formation of an E-olefin depending on the ring size.

First and Second Compounds Comprising a Terminal Olefinic Group, Respectively, and Third Compound Comprising Two Terminal Olefinic Groups The first and the second compound comprise a terminal olefinic group, respectively.

Preferably, the first and the second compound comprise only one terminal olefinic group, respectively.

As the first and second compound, any terminal olefin may be used.

The third compound comprises two terminal olefinic groups.

In a preferred embodiment, the third compound comprises only two terminal olefinic groups.

Regarding the third compound comprising two terminal olefinic groups, in step (Y) a compound has to be used in which the terminal olefinic groups are spaced apart such that a ring closing metathesis reaction between said two terminal groups is possible.

In one embodiment, the two terminal olefinic groups are spaced apart such that by ring-closing metathesis the formation of a 4-membered ring is possible.

In a preferred embodiment, the two olefinic groups are spaced apart such that by ring-closing metathesis the formation of a 5-membered or a 6-membered ring is possible.

In one embodiment, the two terminal olefinic groups are spaced apart such that by ring-closing metathesis the formation of a 7-, 8-, 9-, 10-, 11-, 12-, 13-, 14-, or 15-membered ring or even a higher membered ring is possible. Accordingly, the method according to the invention using step (Y) allows the formation of macrocycles.

As first and second compounds, respectively as third compound, terminal olefins may be used containing carbon and hydrogen only.

However, in a preferred embodiment, the method according to the invention is not restricted to such olefins.

In one embodiment, the first, the second or the third compound respectively comprise one or more hetero atoms. Preferably, said olefins comprise O or N or S or P or halogen, or two or more thereof.

In one embodiment, the first, the second or the third compound comprise one or more functional groups, respectively.

The term "functional group" encompasses any functional group that is known in the art.

In one embodiment, said functional groups may be selected from the group comprising or consisting of: hydroxyl, ether, carboxyl, ester, aldehyde, keto, halogen, amine, amido, imido, or sulfo group or two or more thereof. Moreover, said compounds may contain an internal olefinic group or an alkyne group.

In one embodiment, according to the first aspect, the first and the second compound are independently from one another an alcohol, an ether, a carboxylic acid, a carboxylic ester, an aldehyde, a ketone, a halogen containing compound, an amine, an amide, an imide, a sulfone, a sulfonic acid, an ester of a sulfonic acid, an internal olefin or an alkyne.

In one embodiment, the first and the second compound used in step (X) comprise independently at least one amino acid moiety or at least one peptide moiety.

In one embodiment, said first and second compound are independently represented by the following formula (A):

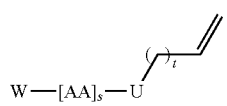

(A)

wherein:
AA is any amino acid moiety;
U is $CH_2$, NH, O, or S;
W is hydrogen, a solid support, a functional group, or a protecting group;
t is 0-10; and
s is 1-10.

In one embodiment, according to the second aspect, the third compound used in step (Y) is an alcohol, an ether, a carboxylic acid, a carboxylic ester, an aldehyde, a ketone, a halogen containing compound, an amine, an amide, an imide, a sulfone, a sulfonic acid, an ester of a sulfonic acid, an internal olefin or an alkyne.

For example, the third compound is a carboxylic ester in which one terminal olefinic group is located in the carboxylic acid moiety, and the other terminal olefinic group is located in the alcohol moiety. The resulting ring-closing metathesis product is a cyclic lactone.

In one embodiment, the third compound used in step (Y) comprises at least one peptide moiety.

In one embodiment, the third compound is represented by the following formula (B):

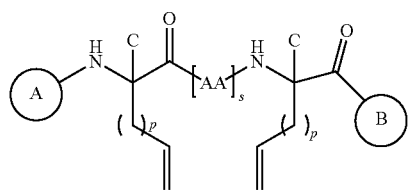

(B)

wherein
AA is any amino acid moiety;
A is independently hydrogen, a functional group, a protecting group, an optionally substituted amino acid residue, an optionally substituted peptide residue, a solid support, or any combination thereof;
B is independently hydrogen, a functional group, a protecting group, an optionally substituted amino acid residue, an optionally substituted peptide residue, a solid support, or any combination thereof;
C is independently H, $C_1$-$C_4$ alkyl, phenyl;
p is independently 1-4; and
s is independently 1-10.

The method according to the invention using a compound of formula (B) in step (Y) may lead to the formation of a stapled peptide. The term "stapled peptide" encompasses peptides in which the peptide folding is fixed such that its conformation is stable. Such peptides are known in the art. They may be valuable products under medical aspects.

Ruthenium Carbene Complexes

The term "ruthenium carbene complex" encompasses all ruthenium complexes comprising a [Ru=C]-moiety.

Examples are e.g. Grubbs catalysts of the first and second generation or other Ru catalysts comprising a [Ru=C]-moiety such as complexes disclosed in WO 2014/201300.

Preferred ruthenium carbene complexes are alkylidene complexes, which preferably are different from a ruthenium methylidene complex, or benzylidene complexes. Said alkylidene or benzylidene groups may be substituted or unsubstituted.

Accordingly, in one embodiment, the ruthenium carbene complex comprises a [Ru=CH($C_1$-$C_4$)]-moiety.

In another embodiment, the ruthenium carbene complex comprises a [Ru=CH($C_6H_5$)]-moiety. The phenyl ring may at least be substituted in ortho position with a $C_1$-$C_4$ alkoxy group.

In one embodiment, the ruthenium carbene complex comprises a [Ru=C($C_1$-$C_4$)$_2$]-moiety.

In another embodiment, the ruthenium carbene complex comprises a [Ru=C($C_6H_5$)$_2$]-moiety.

In another embodiment, the ruthenium carbene complex comprises a [Ru=C(Hal)$_2$]-moiety, wherein Hal is halogen.

In another embodiment, the ruthenium carbene complex comprises a [Ru=C(O—$C_1$-$C_4$ alkyl)$_2$]-moiety.

In another embodiment, the ruthenium carbene complex comprises a [Ru=C=C]-moiety.

Respective complexes are known in the art, or can be prepared according to known methods.

In one embodiment, the complex has the structure of formula I which are known from WO 2014/201300:

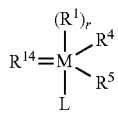

I wherein:
M is ruthenium;
each of $R^1$ and L is independently a neutral ligand;
r is 1-3;
each of $R^4$ and $R^5$ is independently bonded to M through a sulfur or oxygen atom;
$R^{14}$ is a carbene;

$R^4$ and $R^5$ are taken together to form a bidentate ligand, or $R^4$ and $R^5$ are taken together with one or more of $R^1$, L and $R^{14}$ to form a polydentate ligand;

two or more of $R^1$, L and $R^{14}$ are optionally taken together to form a bidentate or polydentate ligand; and each of $R^1$, $R^4$, $R^5$, L and $R^{14}$ is independently and optionally linked to a tag or support.

The term "$R^{14}$ is a carbene" in the structure of formula I encompasses a moiety in which ruthenium and $R^{14}$ form a [Ru=carbene]-moiety.

In one embodiment, said ruthenium carbene complex is of formula I-a:

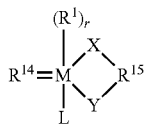

I-a wherein:
M is ruthenium;
each of $R^1$ and L is independently a neutral ligand;
r is 1-3;
each of X and Y is independently —O—, —S—;
$R^{14}$ is a carbene;
$R^{15}$ is —$B^x$:

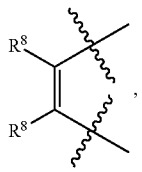

B1

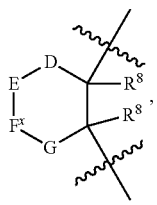

B2

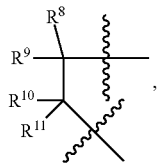

B3

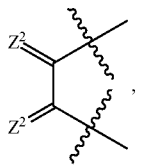

B4

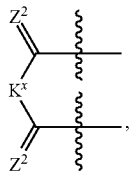

B5

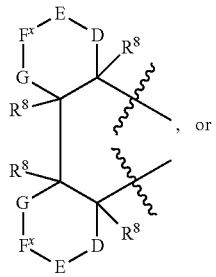

B6

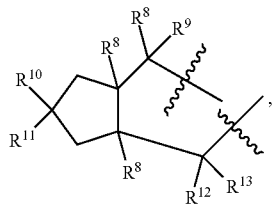

B7 wherein: each $Z^2$ is independently =$C(R^x)2$, =O, =S, =$N(R^x)$;

each of D, E, $F^x$, G is independently —$N(R^8)$—, —$C(R^8)_2$—, —S—, —O—, —$P(R^8)$—, —C(O)—, or —S(O)—;

each of $R^8$, $R^9$, $R^{10}$, $R^{11}$, $R^{12}$, and $R^{13}$ is independently $R^x$, or one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on the same atom to form a =$C(R^x)2$, =$N(R^x)$, =$P(R^x)$, =O, or =S group; or one $R^8$, $R^9$, $R^{10}$, $R^{11}$, $R^{12}$, Or $R^{13}$ is independently taken together with another $R^8$, $R^9$, $R^1$, $R^{11}$, $R^{12}$, or $R^{13}$ on an adjacent atom to form a double bond; or one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms; and $K^x$ is an optionally substituted bivalent $C_{1-20}$ aliphatic or $C_{1-20}$ heteroaliphatic group, wherein 0-6 methylene units are optionally and independently replaced by —O—, —N(R')—, —S—, —C(O)—, —OC(O)—, —C(O)O—, —OC(O)O—, —C(S)—, —OC(S)—, —SC(O)—, —SC(S)—, —S(O)—, —S(O)$_2$—, —OS(O)$_2$O—, —N(R')C(O)—, —C(O)N(R')—, —N(R')C(O)O—, —OC(O)N(R')—, —N(R')C(O)N(R')—, —P($R^x$)—, —P(O)($R^x$)—, or -$Cy^1$-;

each $R^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_{3+}$, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$_2$, —P(O)(OR)$_2$, —SR, —SC(O)R, —S(O)R, —SO$_2$R, —SO$_3$R, or —SO$_2$N(R')$_2$;

each R' is independently R, —C(O)R, —C(O)N(R)$_2$, —C(O)OR, —SO$_2$R, —SO$_2$N(R)$_2$, —P(O)(OR)$_2$, or —OR; and each R is independently hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;

two or more of $R^1$, —X—$R^{15}$—Y—, L and $R^{14}$ are optionally taken together to form a bidentate or polydentate ligand; and each of $R^1$, X, $R^{15}$, Y, L and $R^{14}$ is independently and optionally linked to a tag or support.

The term "neutral ligand" encompasses a ligand which is derived from a charge-neutral precursor. Neutral ligands are represented by e.g. heteroaromatic compounds such as pyridine, phosphines such as tricyclohexylphosphine, or ethers such as THF.

The term "bidentate ligand" encompasses a ligand which is attached to Ru with two sites of the ligand.

The term "polydentate ligand" encompasses a ligand which is attached to Ru with more than two sites of the ligand.

In one embodiment, $R^{14}$ and L are covalently linked, and each of $R^4$ and $R^5$ is bonded to M through sulfur.

In one embodiment, the complex has the structure of formula I':

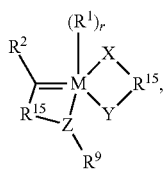

I' wherein:
each of $R^2$ and $R^9$ is independently $R^x$; and
Z is —O—, —S—, —N($R^x$)—, —N=, —P($R^x$)—, —C(O)—, —C(S)—, —S(O)—, or —Z—$R^9$ is halogen.

In one embodiment, the complex has the structure of formula I'':

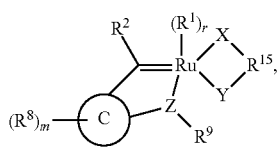

I'' wherein:
each of $R^2$, $R^8$, and $R^9$ is independently $R^x$;
Ring C is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

m is 0-6; and
Z is —O—, —S—, —N($R^x$)—, —N=, —P($R^x$)—, —C(O)—, —C(S)—, —S(O)—, or —Z—$R^9$ is halogen.

In one embodiment, the complex has the structure of formula I-b:

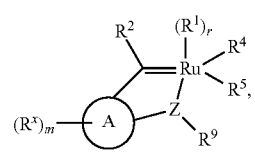

I-b wherein:
each of $R^2$ and $R^9$ is independently $R^x$;
Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur.

In one embodiment, the complex has the structure of formula I-c':

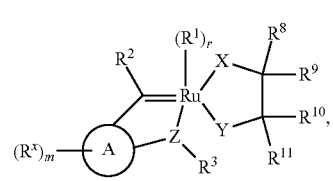

I-c' each of $R^8$, $R^9$, $R^{10}$, $R^{11}$, $R^{12}$, and $R^{13}$ is independently $R^x$, or one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on the same atom to form a =C($R^x$)$_2$, =N($R^x$), =P($R^x$), =O, =S group; or one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on an adjacent atom to form a double bond; or one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms; and $R^3$ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; or —Z—R$^3$ is halogen.

In one embodiment, Z is —O—, —S—, —N(R$^x$)—, —N═, —P(R$^x$)—, —C(O)—, —C(S)—, or —S(O)—, or and R$^9$ is R$^x$; or
wherein —Z—R$^9$ is halogen.

In one embodiment, the complex has the structure of formula I-c:

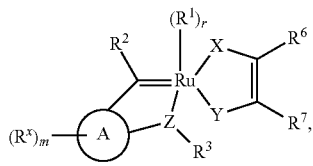

wherein:
each of R$^6$ and R$^7$ is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —Si(R)$_3$, or:
R$^6$ and R$^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur;

In one embodiment, the complex has the structure of formula I-d:

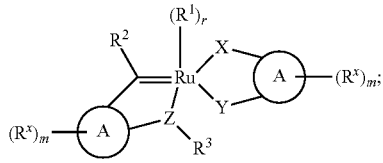

In one embodiment, the complex has the structure of formula I-e:

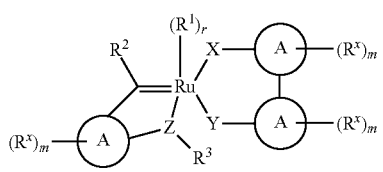

In one embodiment, the complex has the structure of formula I-f:

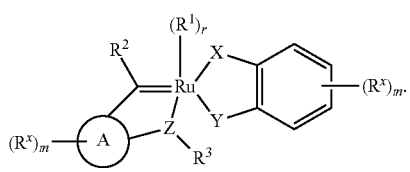

In one embodiment, the complex has the structure of formula I-g:

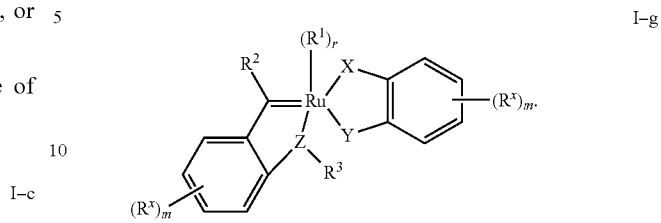

In one embodiment, each of X and Y is —S—.
In another embodiment, one of X or Y is —S—, and one of X or Y is —O—.
In one embodiment, r is 1.
In one embodiment, R$^1$ is a nitrogen containing heterocyclic carbene (NHC). NHCs are known in the art.
In one embodiment, Z is —O—.
In a preferred embodiment, R$^4$ and R$^5$ in formula I form a dithiolate, preferably a catechodithiolate. The term "catechodithiolate" encompasses a catechol in which the hydroxyl groups are replaced by thiol groups, respectively by the anions thereof.
In one embodiment, said carbene is a benzylidene. Preferably, said benzylidene is at least substituted in the phenyl ring in ortho position with a C$_1$-C$_4$ alkoxy group.
In one embodiment, the complex is selected from:

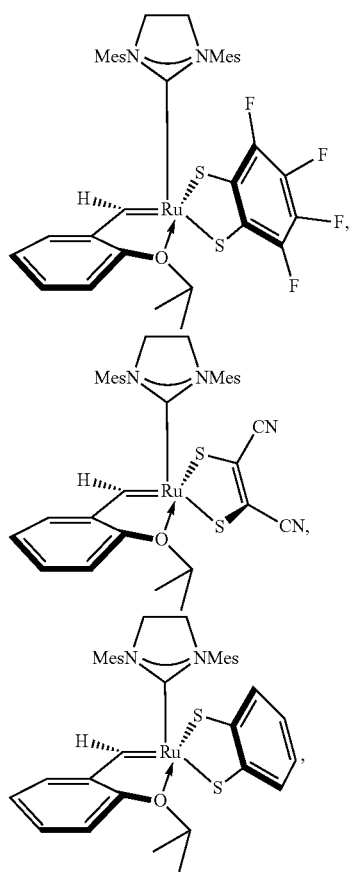

19
-continued
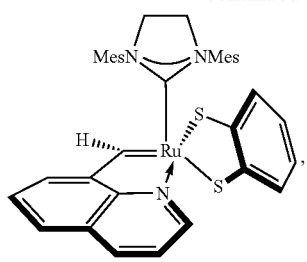
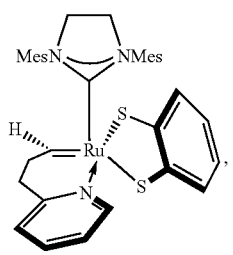
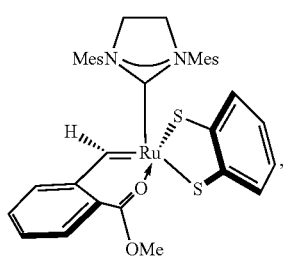
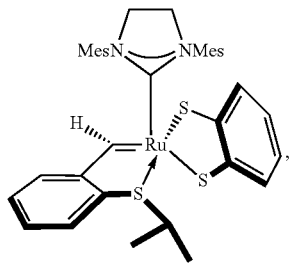
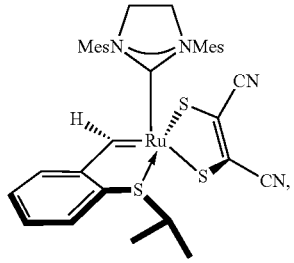
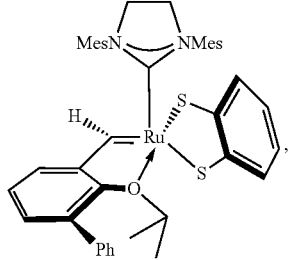
20
-continued
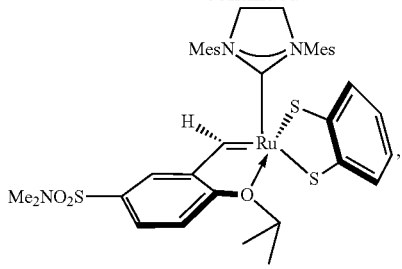
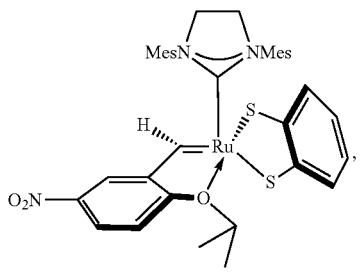
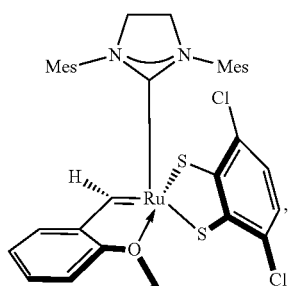
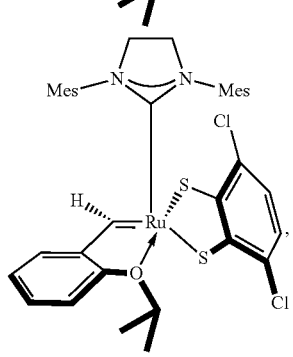
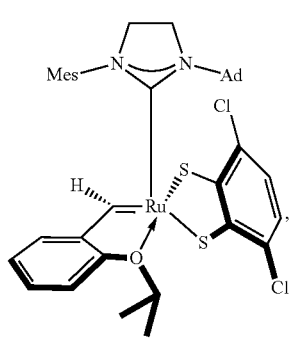

-continued
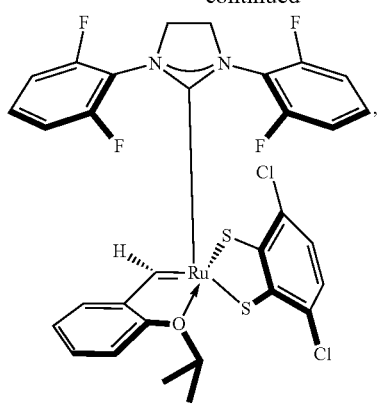
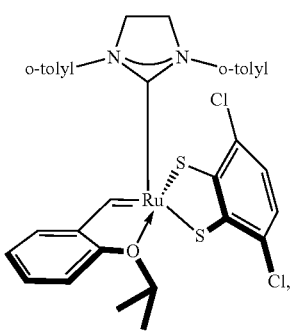
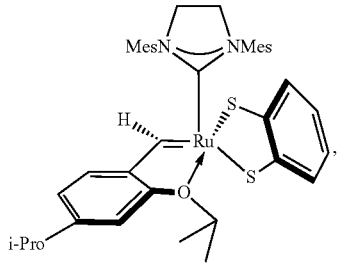
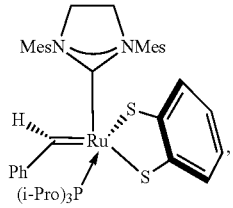
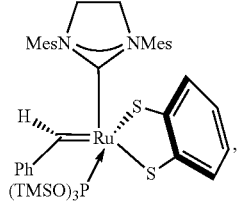
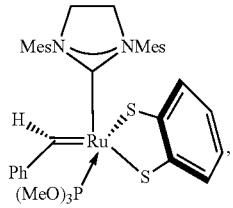
-continued
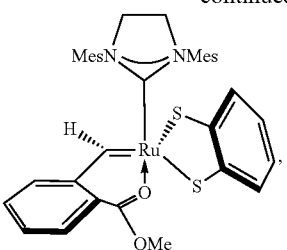
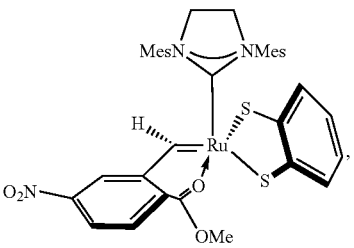
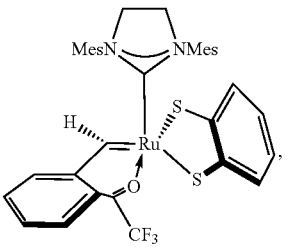
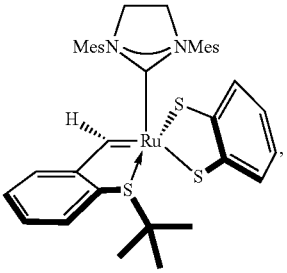
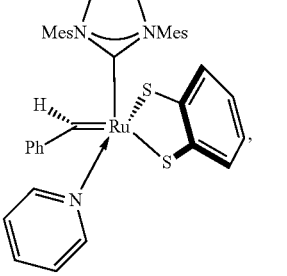
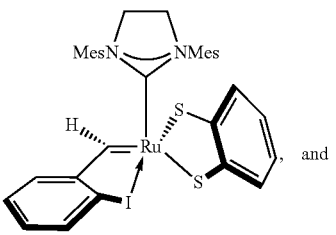, and

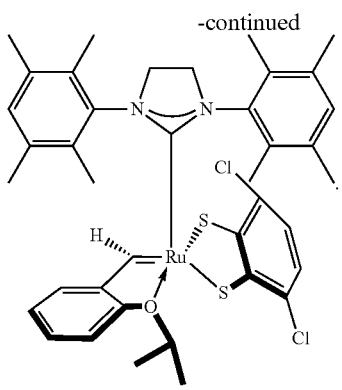

A further complex is of structure

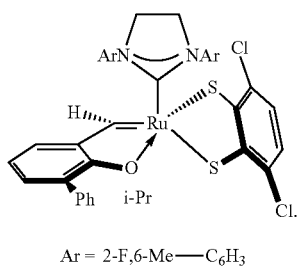

Ar = 2-F,6-Me—C$_6$H$_3$

In one embodiment, the complex is dimerized or polymerized; or the complex is linked to a tag or a solid support.

In another embodiment, the complex is of formula 4 or formula 5

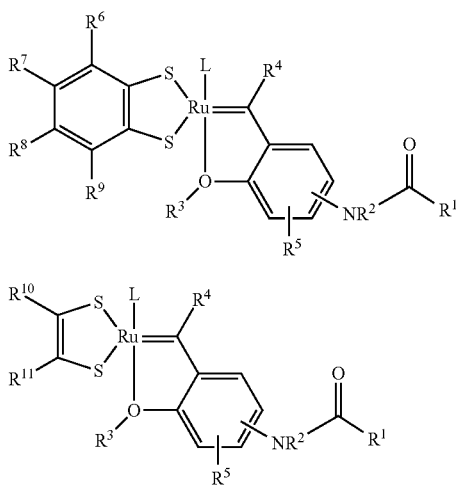

wherein in formula 4 or formula 5 the substituents L and R$^1$, R$^2$, R$^3$, R$^4$, R$^5$, R$^6$, R$^7$, R$^8$, R$^9$, R$^{10}$ and R$^{11}$ have the following meaning:

L is: a neutral ligand;

R$^1$ is: H;

unbranched or branched C$_{1-20}$ alkyl or unbranched or branched C$_{1-20}$ alkoxy; C$_{5-9}$ cycloalkyl or C$_{5-9}$ cycloalkoxy; optionally bearing one or more halogen atoms, respectively; or aryl or aryloxy; optionally substituted, respectively, with one or more of unbranched or branched C$_{1-20}$ alkyl or unbranched or branched C$_{1-20}$ alkoxy, C$_{5-9}$ cycloalkyl or C$_{5-9}$ cycloalkoxy, aryl, aryloxy, unbranched or branched C$_{1-20}$ alkylcarbonyl, arylcarbonyl, unbranched or branched C$_{1-20}$ alkoxycarbonyl, aryloxycarbonyl, heteroaryl, carboxyl, cyano, nitro, amido, aminosulfonyl, N-heteroarylsulfonyl, unbranched or branched C$_{1-20}$ alkylsulfonyl, arylsulfonyl, unbranched or branched C$_{1-20}$ alkylsulfinyl, arylsulfinyl, unbranched or branched C$_{1-20}$ alkylthio, arylthio, sulfonamide, halogen or N(R$^y$)(R$^z$), wherein R$^y$ and R$^z$ are independently selected from H and C$_{1-20}$ alkyl;

R$^2$ is: H; unbranched or branched C$_{1-20}$ alkyl; aryl; —C(O)R$^{12}$; —C(O)OR$^{12}$; —C(O)C(O)R$^{12}$; —C(O)C(O)OR$^{12}$; wherein R$^{12}$ has the meaning of C$_{1-20}$ alkyl or aryl, respectively; R$^{12}$ optionally bearing one or more halogen atoms;

R$^3$ is: unbranched or branched C$_{1-20}$ alkyl; aryl; or R$^{13}$—C(O)—CHR$^{14}$, wherein R$^{13}$ is C$_{1-20}$ alkoxy and R$^{14}$ is H or C$_{1-20}$ alkyl; or wherein R$^{13}$ is C$_{1-20}$ alkoxy and R$^{14}$ is C(O)—O—C$_{1-20}$ alkyl; or wherein R$^{13}$ is C$_{1-20}$ alkyl and R$^{14}$ is H; or R$^{13}$ is OH and R$^{14}$ is H or C$_{1-20}$ alkyl; or R$^{15}$—O—N(R$^{16}$)—C(O)—CHR$^{17}$, wherein R$^{15}$, R$^{16}$, and R$^{17}$ are independently H or C$_{1-20}$ alkyl;

R$^4$ is: H;

R$^5$, R$^6$, R$^7$, R$^8$, R$^9$, R$^{10}$ and R$^{11}$ are, independently, H; unbranched or branched C$_{1-20}$ alkyl or unbranched or branched C$_{1-20}$ alkoxy; C$_{5-9}$ cycloalkyl or C$_{5-9}$ cycloalkoxy; aryl; aryloxy; unbranched or branched C$_{1-20}$ alkylcarbonyl; arylcarbonyl; unbranched or branched C$_{1-20}$ alkoxycarbonyl; aryloxycarbonyl; heteroaryl; carboxyl; cyano; nitro; amido; aminosulfonyl; N-heteroarylsulfonyl; unbranched or branched C$_{1-20}$ alkylsulfonyl; arylsulfonyl; unbranched or branched C$_{1-20}$ alkylsulfinyl; arylsulfinyl; unbranched or branched C$_{1-20}$ alkylthio; arylthio; sulfonamide; halogen; or N(R$^y$)(R$^z$), wherein R$^y$ and R$^z$ are independently selected from H and C$_{1-20}$ alkyl; or aryl or aryloxy, respectively substituted with one or more of unbranched or branched C$_{1-20}$ alkyl or unbranched or branched C$_{1-20}$ alkoxy, C$_{5-9}$ cycloalkyl or C$_{5-9}$ cycloalkoxy, aryl, aryloxy, unbranched or branched C$_{1-20}$ alkylcarbonyl, arylcarbonyl, unbranched or branched C$_{1-20}$ alkoxycarbonyl, aryloxycarbonyl, heteroaryl, carboxyl, cyano, nitro, amido, aminosulfonyl, N-heteroarylsulfonyl, unbranched or branched C$_{1-20}$ alkylsulfonyl, arylsulfonyl, unbranched or branched C$_{1-20}$ alkylsulfinyl, arylsulfinyl, unbranched or branched C$_{1-20}$ alkylthio, arylthio, sulfonamide, halogen or N(R$^y$)(R$^z$), wherein R$^y$ and R$^z$ are independently selected from H and C$_{1-20}$ alkyl.

In one embodiment, in formula 4 or 5 the neutral ligand L is

P(R$^x$)$_3$, wherein R$^x$ is independently branched or unbranched C$_{1-20}$ alkyl or C$_{1-20}$ alkoxy, C$_{5-9}$ cycloalkyl, or aryl; or RCN, wherein R is branched or unbranched C$_{1-20}$ alkyl, C$_{5-9}$ cycloalkyl, or aryl; or a carbene containing the moiety of formula 6

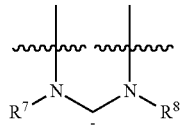

wherein R⁷ and R⁸ as defined in formula 6 are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen.

In one embodiment, L in formula 4 or 5 is a nitrogen-containing heterocyclic carbene (NHC) of one of formulas 6a, 6b, 6c or 6d:

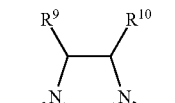

6a

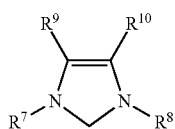

6b

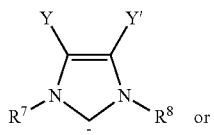

6c or

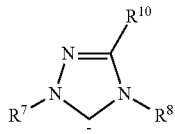

6d wherein R⁹ and R¹⁰ are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$ alkoxy or halogen; or
R⁹ and R¹⁰ together with the carbon atoms to which they are attached are combined to form a carbocyclic 3 to 8 membered ring;
Y and Y' are halogen.

In one embodiment, R¹ is $C_{1-6}$ alkyl, optionally substituted with one or more of halogen; or phenyl, optionally substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

In one embodiment, R² is H.
In one embodiment, NR²—C(O)—R¹ is in para-position with respect to O.
In one embodiment, R³ is methyl or isopropyl.
In one embodiment, R⁵ is H.
In one embodiment, R⁶, R⁷, R⁸, and R⁹ in formula 4 are independently selected from H and halogen.

In one embodiment, R¹⁰ and R¹¹ as defined in formula 5 are independently selected from halogen and cyano.

In one embodiment, L is of formula 6a or 6b, preferably wherein R⁹ and R¹⁰ as defined in formula 6a or 6b are H, respectively, and R⁷ and R⁹ as defined in formula 6a and 6b are mesityl, or 2,6-diisopropylphenyl; or wherein L is of formula

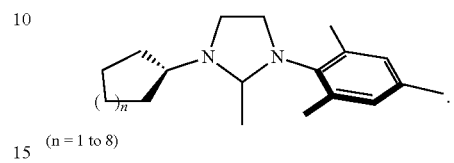

(n = 1 to 8)

In one embodiment, the compound is immobilized on a solid support.

In one embodiment, the nitrogen-containing carbene (NHC) is of formula 7:

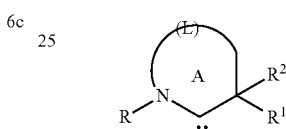

7 wherein the A-ring is a 4-, 5-, 6-, or 7-membered ring; and L in formula 7 is a linking group representing from one to four ring vertices selected from carbon with available valences optionally occupied by hydrogen or optionally substituted by $C_{1-10}$ alkyl and aryl, optionally substituted. These nitrogen-containing carbenes are known from WO 2006/138166.

R in formula 7 represents a member selected from $C_{1-10}$ alkyl and aryl, optionally substituted. The symbols R¹ and R² in formula 7 represent independently members selected from $C_{1-10}$ alkyl and aryl, optionally substituted.

In a preferred embodiment, the nitrogen-containing carbene is of formula 7a or 7b:

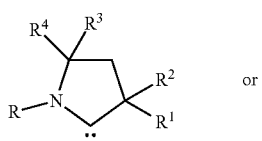

7a or

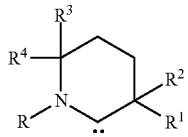

7b wherein R, R¹, R², R³ and R⁴ in formulae 7a and 7b independently represent a member selected from $C_{1-10}$ alkyl and aryl, optionally substituted.

It should be noted that the nitrogen-containing carbenes falling under formula 6 and 7 may also be contained in the structure of formula I which is known from WO 2014/201300 (termed as R¹ in this structure of formula I).

In one embodiment, the complex is selected from compounds E1 to E11 falling under the general formulas 4 or 5

E1 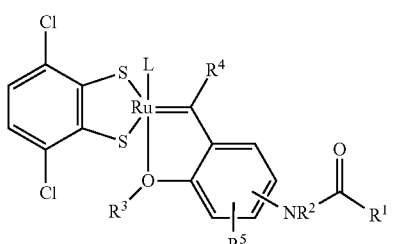
E2 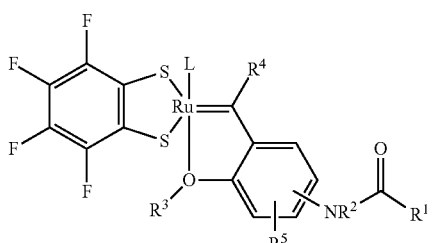
E3 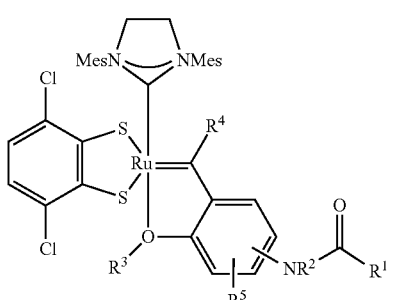
E4 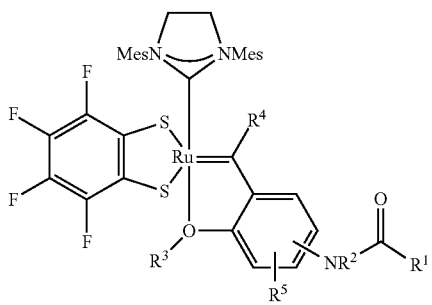
E5 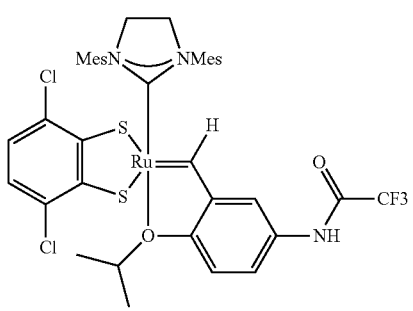
-continued
E6 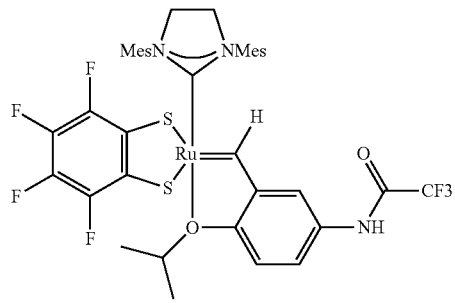
E7 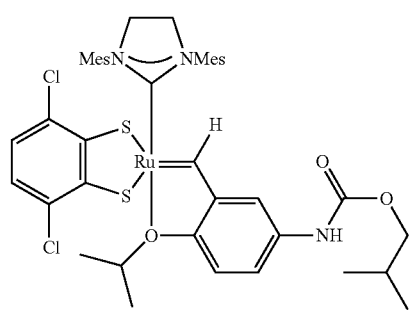
E8 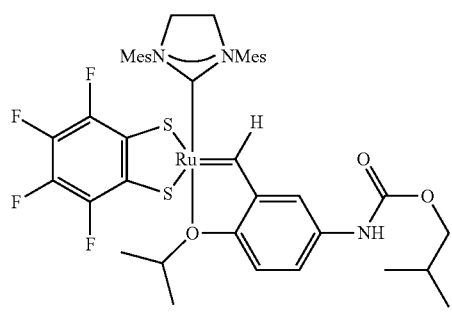
E9 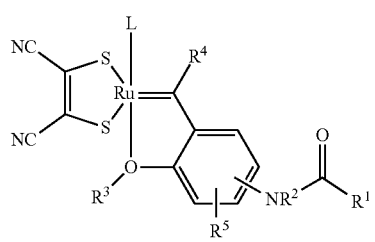
E10 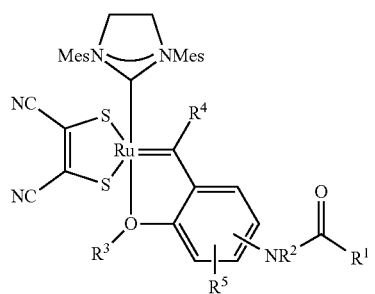

-continued

E11

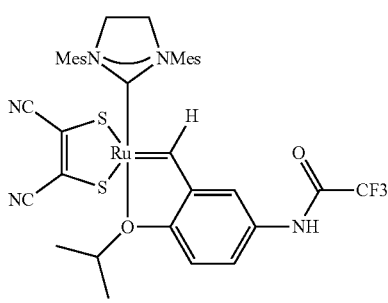

The amide function NR²—C(O)—R¹ in formula 4 and formula 5 can act as a spacer for the introduction of an ion marker ("tag") for immobilization in an aqueous and/or ion phase as well as on a solid support. Such an ion marking enables better recycling of the catalytic complexes to be performed in aqueous/ion solvents or on a solid support (continuous flow reaction) and thus enables a clear reduction in the cost of the reaction while avoiding contamination of high added value products, in particular in the context of a pharmaceutical molecule synthesis process.

Accordingly, in one embodiment, the compound of formula 4 or 5 is immobilized in an aqueous and/or ion phase or on a solid support.

In another embodiment, the complex is of one of the following structures:

wherein

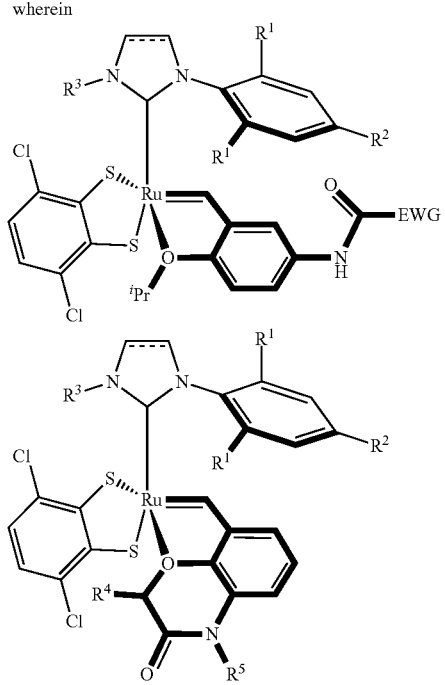

$R^1$ = Me, $^i$Pr. $R^2$ = Me, H. $R^3$ = Ar, Cycloalkyl.
$R^4$ = Alkyl. $R^5$ = H, C(O)EWG, and EWG is an electron-withdrawing group.

Preferably, Ar is phenyl, optionally substituted with one or more of unbranched or branched $C_{1-20}$ alkyl or unbranched or branched $C_{1-20}$ alkoxy, or halogen.

Further preferably, Alkyl is unbranched or branched $C_{1-20}$ alkyl.

In a third aspect, the invention relates to the use of an internal olefin as defined in the first or second aspect for reducing activity loss of a Ru carbene complex comprising a [Ru=C]-moiety when using said complex in a metathesis reaction in which ethylene is developed.

Accordingly, the invention relates to a method of reducing activity loss of a Ru carbene complex comprising a [Ru=C]-moiety when using said complex in a metathesis reaction in which ethylene is developed, the method comprising step (V):

(V) performing said reaction in the presence of an internal olefin.

In a preferred embodiment said internal olefin is Z-2-butene.

The reactions according to step (X) and step (Y), respectively step (V), may be carried out according to process conditions which are basically known in the art of making metathesis reactions.

EXAMPLES

Example 1

General Procedure for Cross-Metathesis Between Two Terminal Olefins which May be the Same or which May be Different from One Another According to Step (X) (Method According to the First Aspect)

In a N₂-filled glovebox, an oven-dried vial equipped with a magnetic stir bar is charged with the alkene substrates (1:3 ratio), unpurified Z-2-butene (3) and a solution of the appropriate amount of catechothiolate complex Ru-2 (WO 2014/201300)

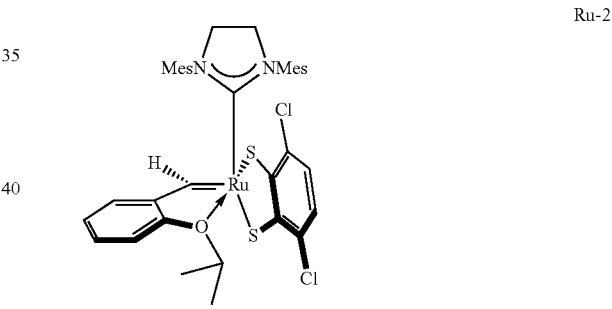

Ru-2 dissolved in THF. The reaction vessel is then sealed. The mixture is allowed to stir at 22° C. for 4 h, after which the volatiles are removed in vacuo (typically, 100 torr for 2 mins). The flask containing the residue is then charged with a solution of the appropriate amount of Ru-2 in THF and the system is placed under 100 torr of vacuum. The resulting solution is allowed to stir for 8 h at 22° C., after which the reaction is quenched by the addition of wet (undistilled) diethyl ether and the volatiles were removed in vacuo. Purification may be performed by silica gel chromatography.

The following examples show the effectiveness of the method using as internal olefin according to steps (X), (Y) or (V) Z-2-butene (3). For example, biologically active compounds such as prostaglandins may be prepared:

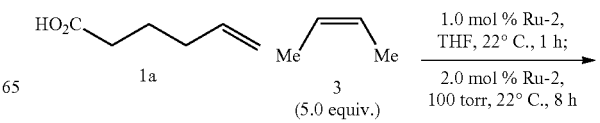

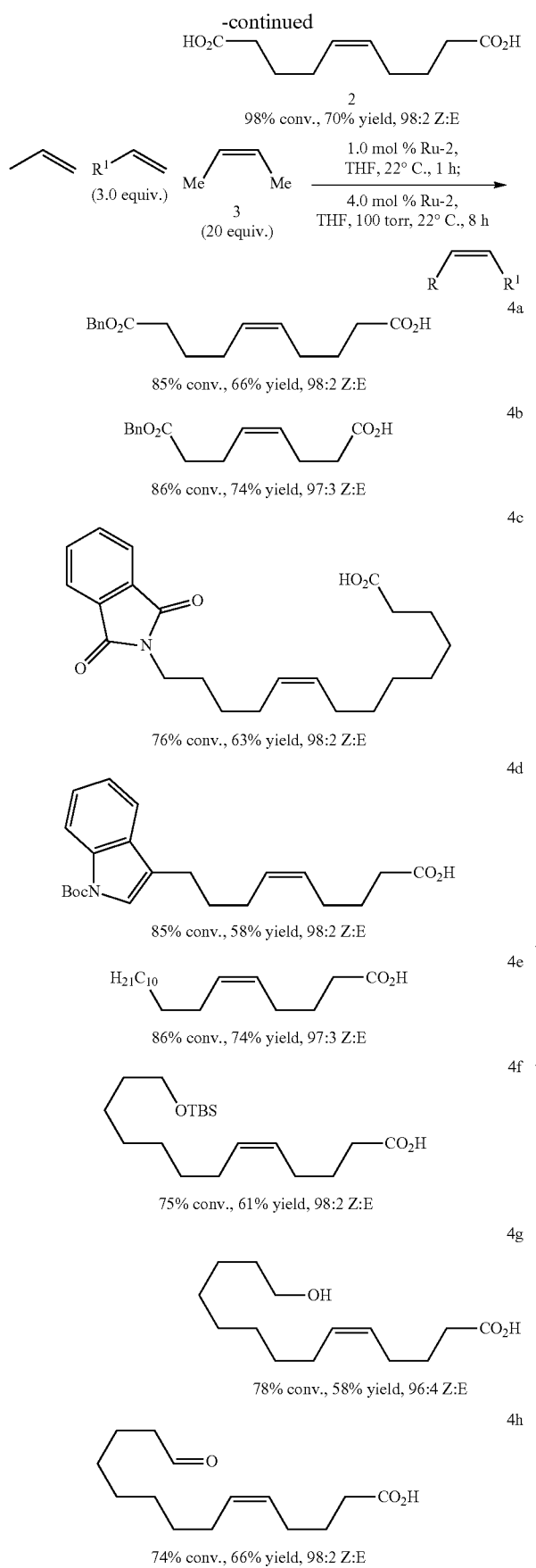
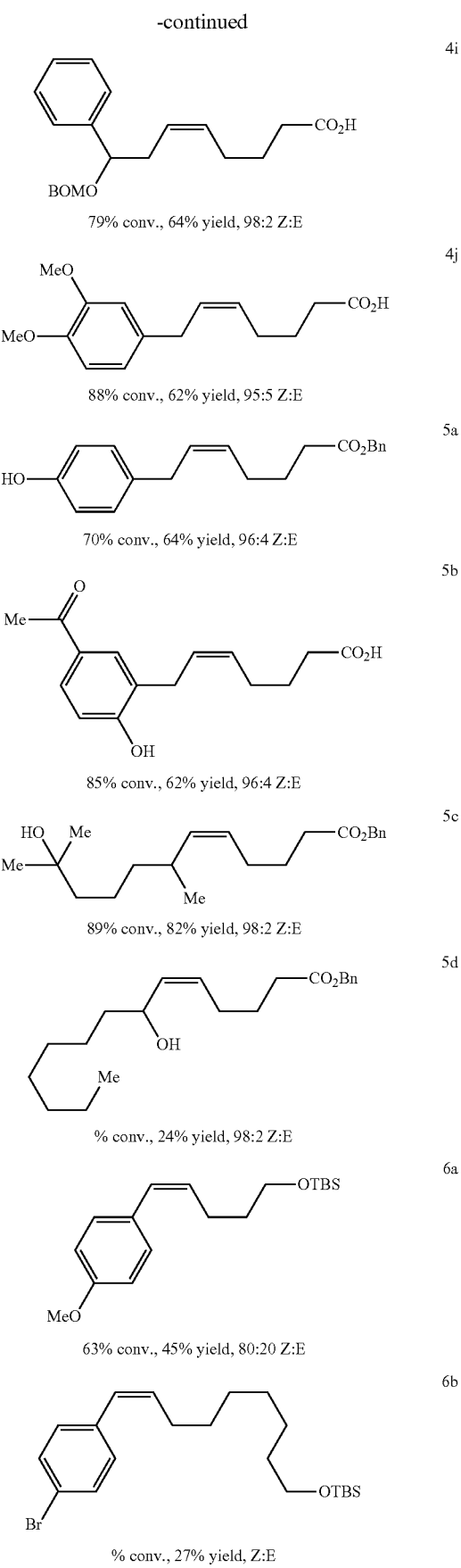

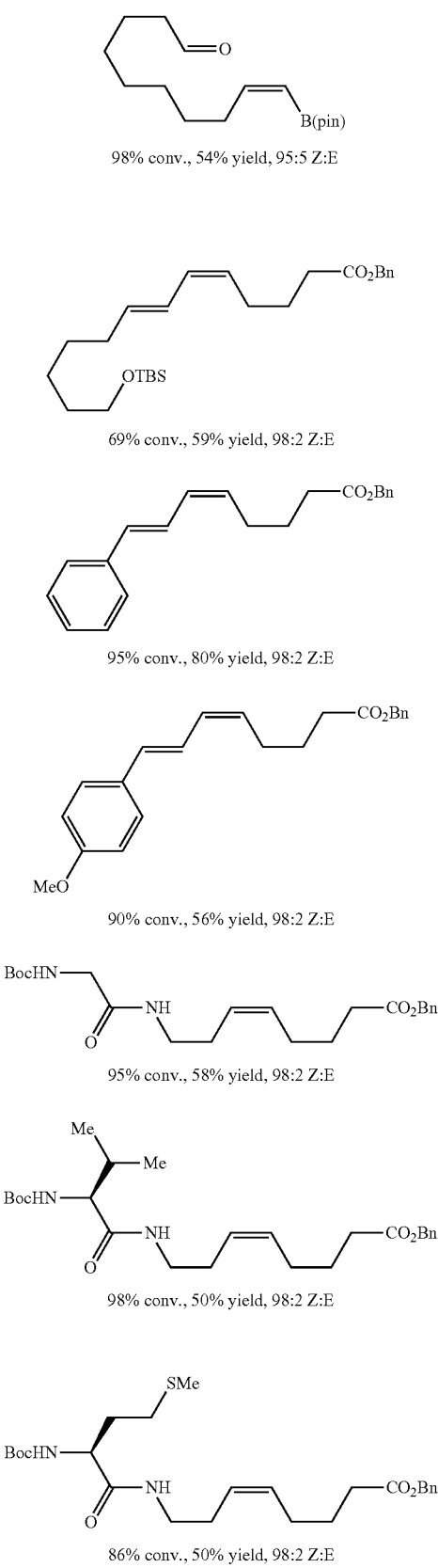
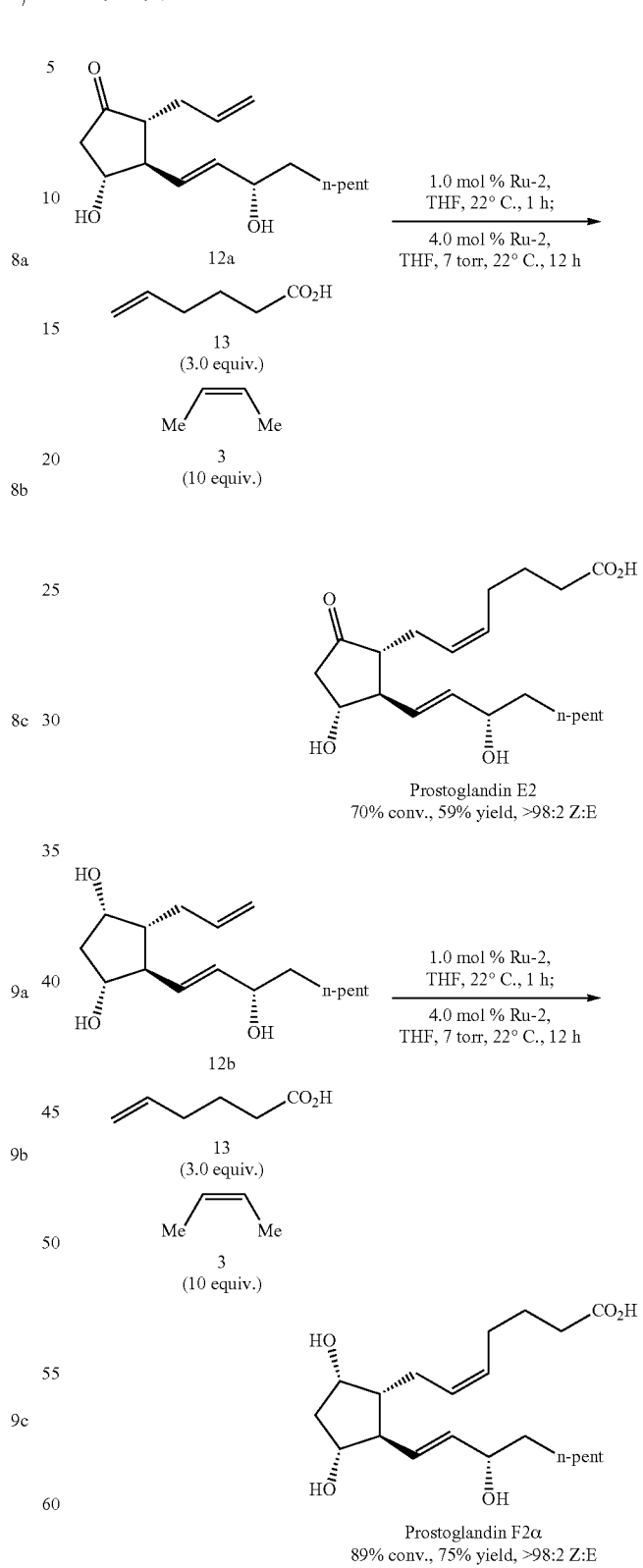
(Bn=benzyl; Boc=tert-butoxycarbonyl; TBS=tert-butyldimethylsilyl)
The following further compounds prepared according to the method of the invention have been published (Xu C et al, J. Am. Chem. Soc, 2017 Aug. 9; 139(31): 10919-10928):

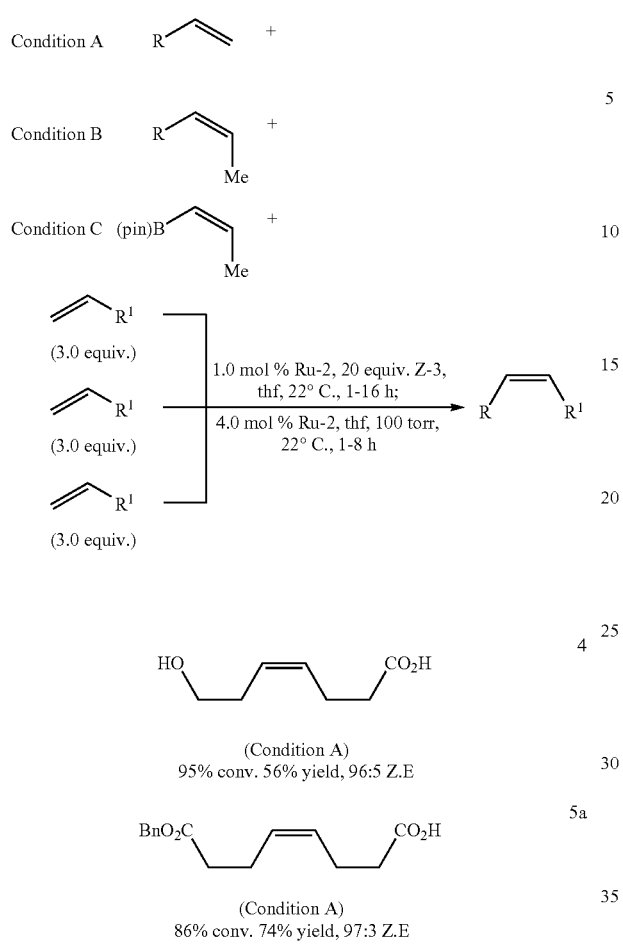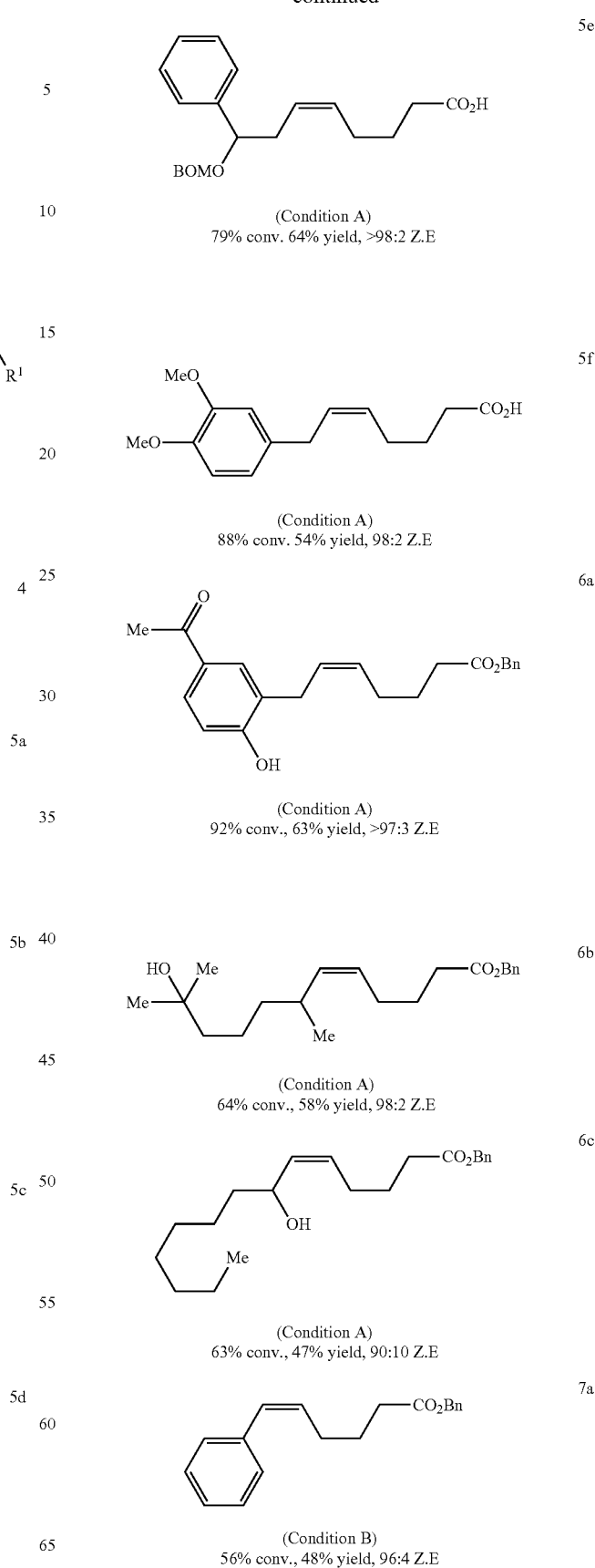

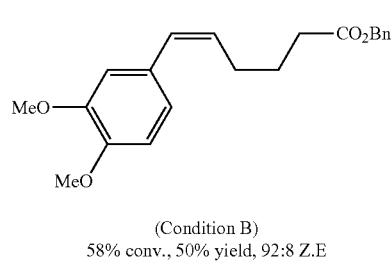
(Condition B)
58% conv., 50% yield, 92:8 Z:E
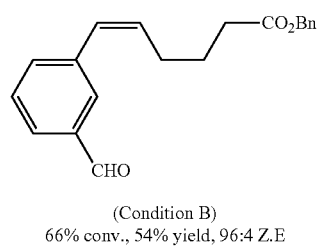
(Condition B)
66% conv., 54% yield, 96:4 Z:E
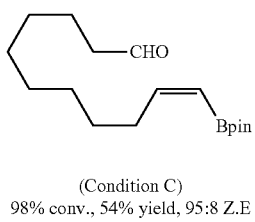
(Condition C)
98% conv., 54% yield, 95:8 Z:E
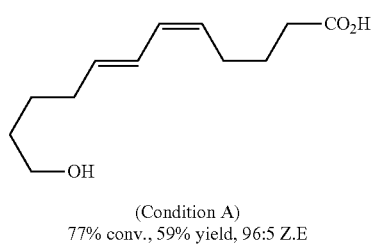
(Condition A)
77% conv., 59% yield, 96:5 Z:E
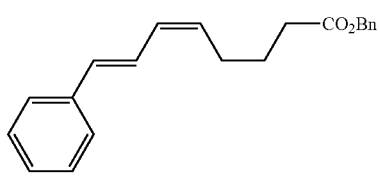
(Condition A)
95% conv., 80% yield, 97:3 Z:E
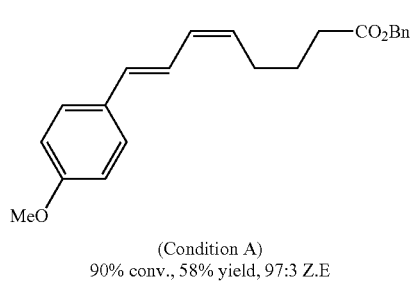
(Condition A)
90% conv., 58% yield, 97:3 Z:E
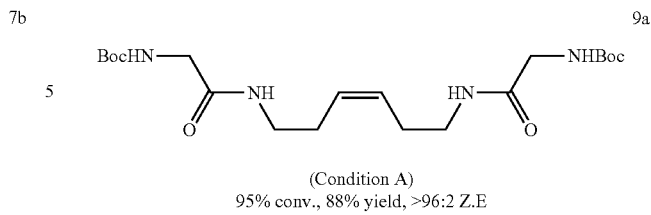
(Condition A)
95% conv., 88% yield, >96:2 Z:E
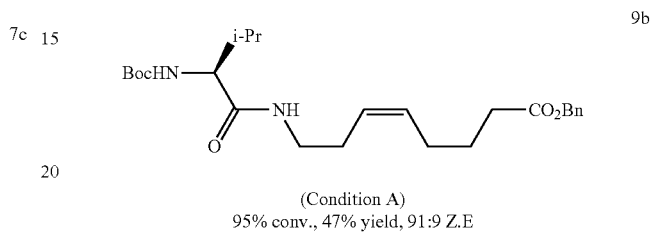
(Condition A)
95% conv., 47% yield, 91:9 Z:E
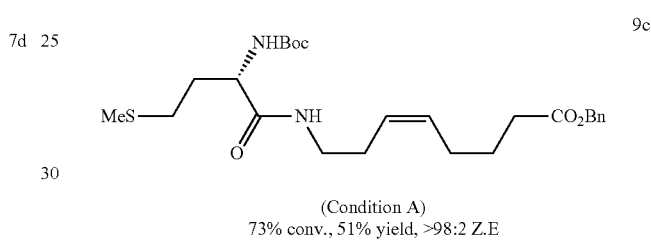
(Condition A)
73% conv., 51% yield, >98:2 Z:E
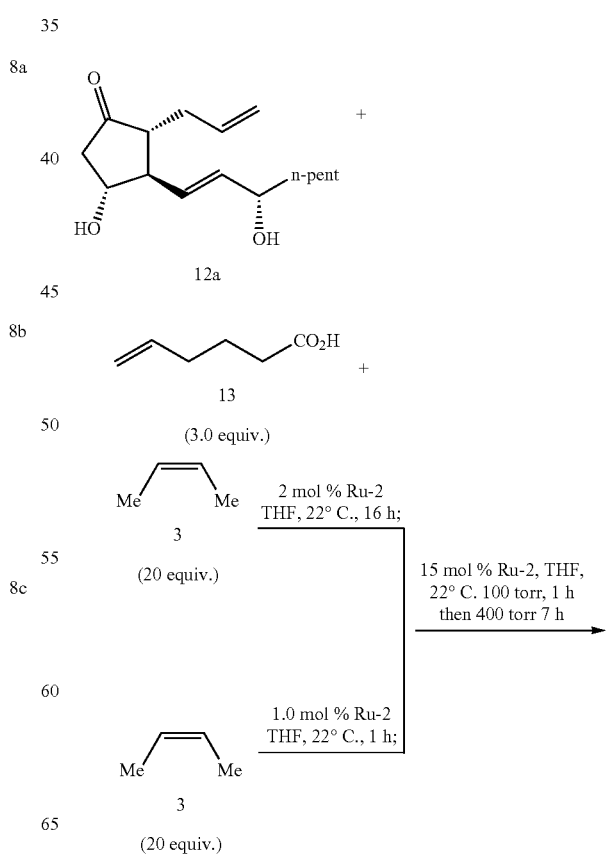

39
-continued

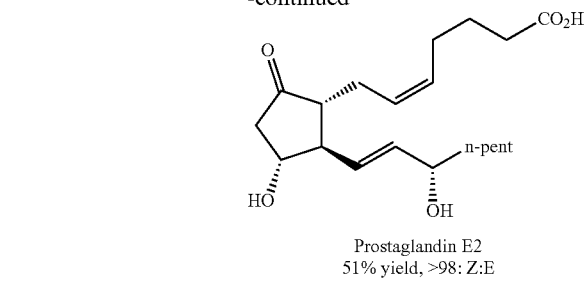

Prostaglandin E2
51% yield, >98: Z:E

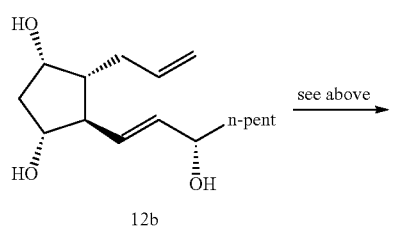

12b see above →

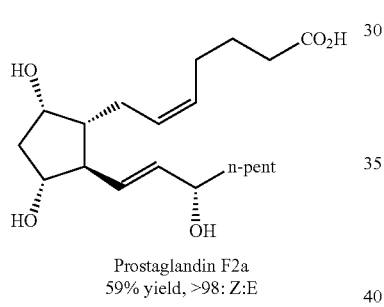

Prostaglandin F2a
59% yield, >98: Z:E

The following example of a kinetically controlled E-selective cross-metathesis published in J. Am. Chem. Soc, 2017 Aug. 9; 139(31): 10919-10928 evidences the effectiveness of the method according to the invention using as internal olefin according to steps (X), (Y) or (V) E-2-butene:

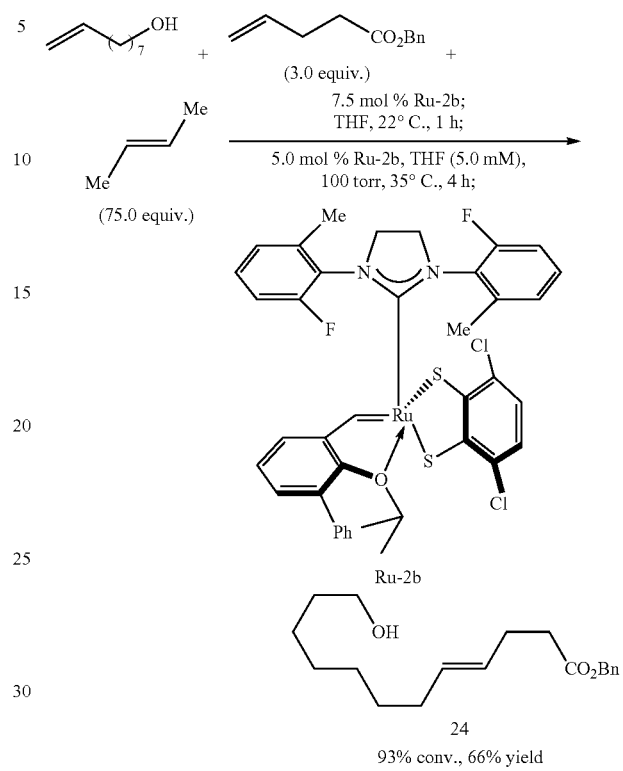

24
93% conv., 66% yield
96:4 E:Z

Example 2

General Procedure for Macrocyclic Ring-Closing Metathesis (RCM) Represented by the Synthesis of (5R,8R,Z)-Methyl-5-benzyl-14-((S)-2-((tert-butoxycarbonyl)amino)-3-(4-hydroxyphenyl)propanamido)-3,6,15-trioxo-1,4,7-triazacyclopentadec-10-ene-8-carboxylate (15) Prepared According to the Following Scheme (Method According to the Second Aspect):

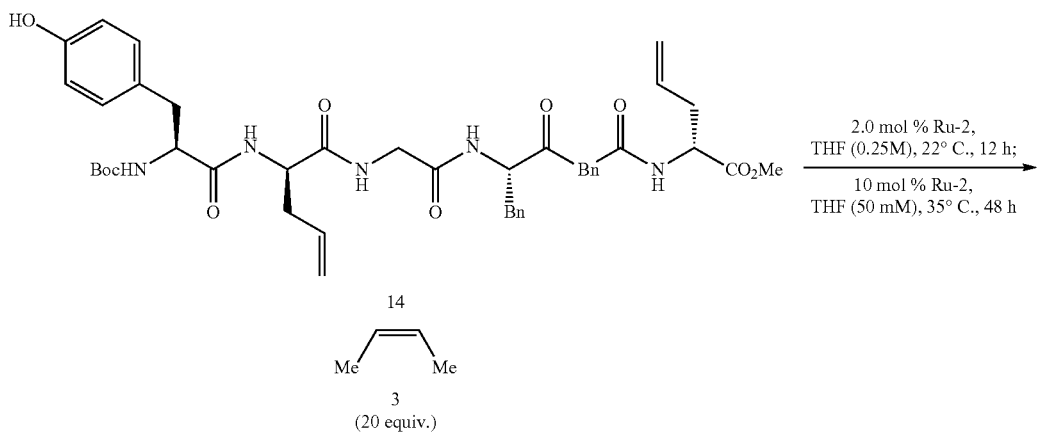

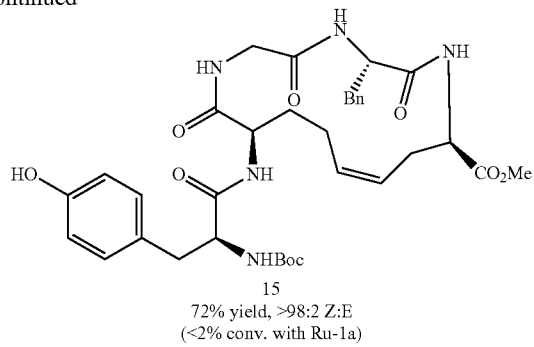

15
72% yield, >98:2 Z:E
(<2% conv. with Ru-1a)

In a $N_2$-filled glove box, a solution of unpurified Z-2-butene (3) in THF (171 mg, 1.00 mmol) was added to an oven-dried vial containing (6S,9R,15S,18R)-methyl-9,18-diallyl-15-benzyl-6-(4-hydroxybenzyl)-2,2-dimethyl-4,7,10,13,16-pentaoxo-3-oxa-5,8,11,14,17-pentaazanonadecan-19-oate (14; 34.7 mg, 0.050 mmol), followed by a THF solution of Ru-2 (0.76 mg, 0.001 mmol in 200 mL THF). The vessel was sealed and the mixture was allowed to stir for 1 h at 22° C. Volatiles were then removed in vacuo and the resulting black solid residue was dissolved in THF (800 mL) and a solution of Ru-2 was added (3.78 mg, 0.005 mmol in 200 mL THF). The resulting solution was allowed to stir for 48 h at 35° C. The reaction was then quenched by the addition of wet (undistilled) diethyl ether and the volatiles were removed in vacuo. The resulting black solid residue was purified by silica gel chromatography (1-3% MeOH in $CH_2Cl_2$).

Compound 15 may be regarded as a stapled peptide.

It is noteworthy to mention that if compound 15 is prepared in the presence of Grubbs catalyst Ru-1a

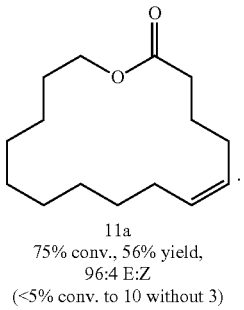

Ru-1a however in the absence of internal olefin Z-2-butene, conversion is low.

The following compound was correspondingly prepared in a macrocyclisation reaction, wherein a high Z-selectivity was achieved:

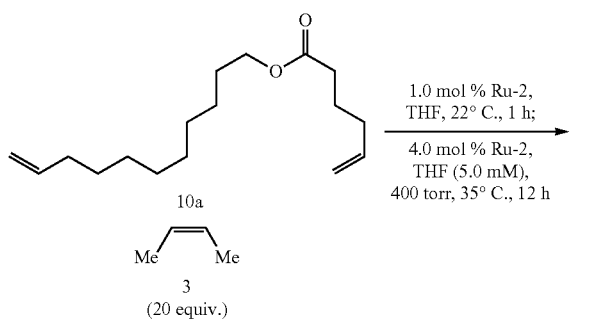

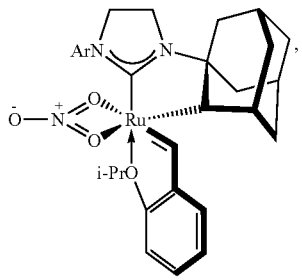

11a
75% conv., 56% yield,
96:4 E:Z
(<5% conv. to 10 without 3)

In turn, without the addition of an internal olefin such as Z-2-butene, the conversion of compound 10a to compound 11a proceeds to 5% only compared to 75% conversion if the reaction is carried out in the presence of said internal olefin.

The following macrocycles 11 b to 11 j were prepared using respective starting materials and the method according to the invention:

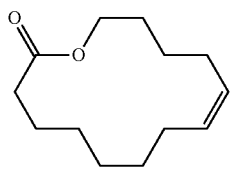

11b

82% conv., 67% yield,
98:2 Z:E

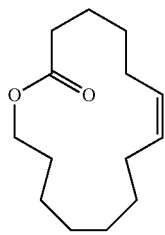

11c

86% conv.,
67% yield,
98:2 Z:E

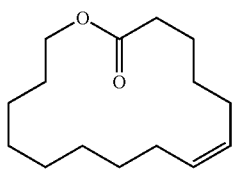

81% conv., 70% yield,
98:2 Z:E

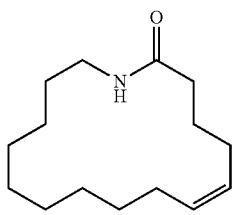

82% conv., 55% yield,
98:2 Z:E

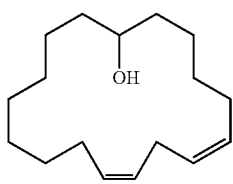

87% conv., 53% yield,
96:4 Z:E

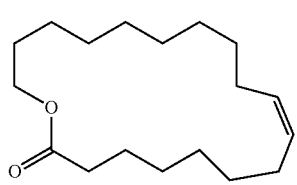

81% conv., 65% yield,
98:2 Z:E

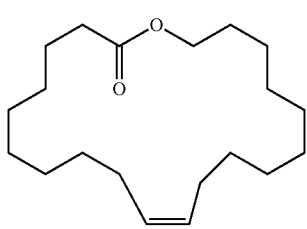

84% conv., 60% yield,
96:4 Z:E

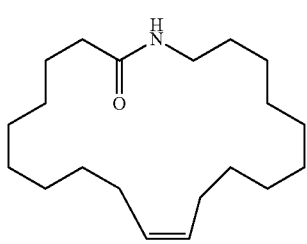

90% conv., 57% yield,
98:2 Z:E

11d

11e

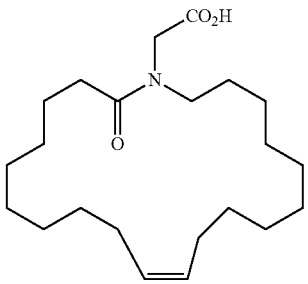

62% conv., 40% yield,
97:3 Z:E

An example of a kinetically controlled macrocyclisation published in J. Am. Chem. Soc, 2017 Aug. 9; 139(31): 10919-10928) prepared according to the method of the invention is depicted below:

11f

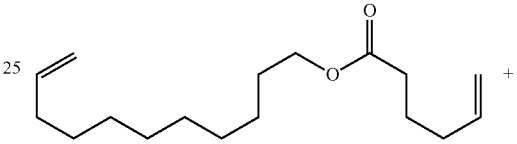

11a

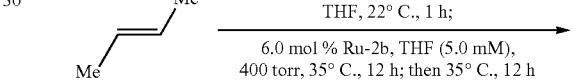

11g

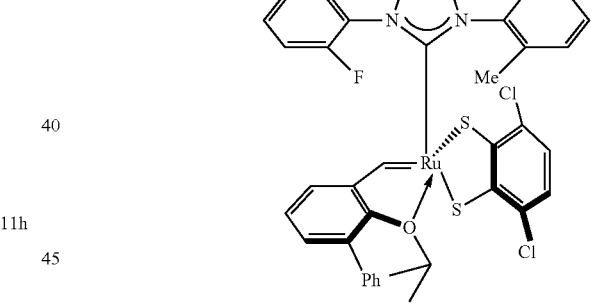

Ru-2b

11h

11i

E-12a
77% conv. 52% yield
95:5 E:Z

The invention claimed is:

1. A method of making a cross metathesis product, the method comprising at least step (X) or step (Y):

(X) reacting in a cross metathesis reaction a first compound comprising a terminal olefinic group with a second compound comprising a terminal olefinic group, wherein the first and the second compound may be identical or may be different from one another; or (Y) reacting in a ring-closing metathesis reaction two terminal olefinic groups which are comprised in a third compound;
wherein the reacting in step (X) or step (Y) is performed in the presence of a ruthenium carbene complex comprising a [Ru═C]-moiety and an internal olefin which may be a Z-olefin or an E-olefin.

2. The method of claim 1, wherein more than 1 equivalent of said internal olefin is employed per equivalent of said first or second compound, respectively said third compound.

3. The method of claim 1, further comprising step (Z) after step (X) or step (Y):
(Z) removing said internal olefin and/or a metathesis product which is formed from said internal olefin in step (X) or step (Y).

4. The method of claim 1, wherein said internal olefin is a $C_{4-8}$ olefin.

5. The method of claim 1, wherein said internal olefin is Z-2-butene or E-2-butene.

6. The method of claim 1, wherein the first, the second or the third compound respectively comprise one or more functional groups.

7. The method of claim 1, wherein the first and the second compound are independently from one another an alcohol, an ether, a carboxylic acid, an ester, an aldehyde, a ketone, a halogen containing compound, an amine, an amide, an imide, a sulfone, a sulfonic acid, an ester of a sulfonic acid, an internal olefin or an alkyne; or wherein the third compound is an alcohol, an ether, a carboxylic acid, an ester, an aldehyde, a ketone, a halogen containing compound, an amine, an amide, an imide, a sulfone, a sulfonic acid, an ester of a sulfonic acid, an internal olefin or an alkyne.

8. The method of claim 1, wherein the first and the second compound used in step (X) comprise independently an amino acid moiety or a peptide moiety.

9. The method of claim 1, wherein the third compound used in step (Y) comprises a peptide moiety.

10. The method of claim 9, wherein the third compound used in step (C) is of formula (B)

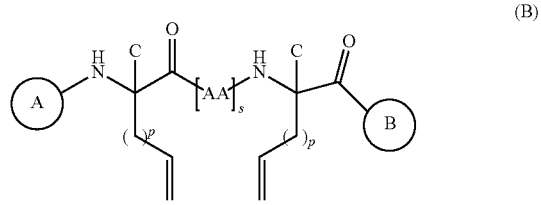

(B)

wherein
AA is any amino acid moiety;
A is independently hydrogen, a functional group, a protecting group, an optionally substituted amino acid residue, an optionally substituted peptide residue, a solid support, or any combination thereof;
B is independently hydrogen, a functional group, a protecting group, an optionally substituted amino acid residue, an optionally substituted peptide residue, a solid support, or any combination thereof;
C is independently H, $C_1$-$C_4$ alkyl, phenyl;
p is independently 1-4; and
s is independently 1-10.

11. The method of claim 10, wherein the peptide formed by ring-closing metathesis of the compound of formula (B) is a stapled peptide.

12. The method of claim 1, wherein said ruthenium carbene complex comprising a [Ru═C]-moiety is of formula I:

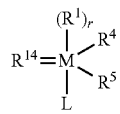

I wherein:
M is ruthenium;
each of $R^1$ and L is independently a neutral ligand;
r is 1-3;
each of $R^4$ and $R^5$ is independently bonded to M through a sulfur or oxygen atom;
$R^{14}$ is a carbene;
$R^4$ and $R^5$ are taken together to form a bidentate ligand, or $R^4$ and $R^5$ are taken together with one or more of $R^1$, L and $R^{14}$ to form a polydentate ligand;
two or more of $R^1$, L and $R^{14}$ are optionally taken together to form a bidentate or polydentate ligand; and
each of $R^1$, $R^4$, $R^5$, L and $R^{14}$ is independently and optionally linked to a tag or support.

13. The method of claim 12, wherein $R^4$ and $R^5$ form a dithiolate.

14. The method of claim 12, wherein said carbene $R^{14}$ is a benzylidene.

15. The method of claim 12, wherein $R^1$ is a nitrogen-containing heterocyclic carbene and r=1.

16. The method of claim 1, wherein the complex is of formula 4 or formula 5

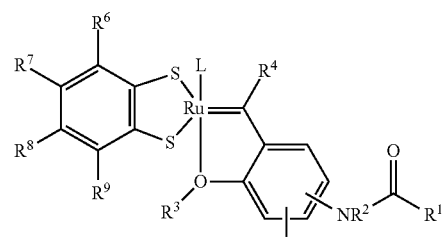

4

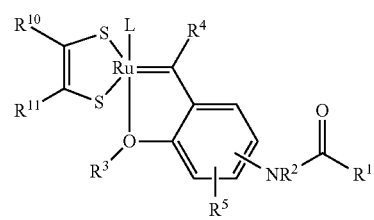

5 wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:
L is: a neutral ligand;
$R^1$ is: H;
unbranched or branched $C_{1-20}$ alkyl or unbranched or branched $C_{1-20}$ alkoxy; $C_{5-9}$ cycloalkyl or $C_{5-9}$ cycloalkoxy; optionally bearing one or more halogen atoms, respectively; or
aryl or aryloxy; optionally substituted, respectively, with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;

$R^2$ is: H; unbranched or branched $C_{1-20}$ alkyl; aryl; —$C(O)R^{12}$; —$C(O)OR^{12}$; —$C(O)C(O)R^{12}$; —$C(O)C(O)OR^{12}$; wherein $R^{12}$ has the meaning of $C_{1-20}$ alkyl or aryl, respectively; $R^{12}$ optionally bearing one or more halogen atoms;

$R^3$ is: unbranched or branched $C_{1-20}$ alkyl; aryl; or $R^{13}$—$C(O)$—$CHR^{14}$, wherein $R^{13}$ is $C_{1-20}$ alkoxy and $R^{14}$ is H or $C_{1-20}$ alkyl; or wherein $R^{13}$ is $C_{1-20}$ alkoxy and $R^{14}$ is $C(O)$—O—$C_{1-20}$ alkyl; or wherein $R^{13}$ is $C_{1-20}$ alkyl and $R^{14}$ is H; or $R^{13}$ is OH and $R^{14}$ is H or $C_{1-20}$ alkyl; or $R^{15}$—O—$N(R^{16})$—$C(O)$—$CHR^{17}$, wherein $R^{15}$, $R^{16}$, and $R^{17}$ are independently H or $C_{1-20}$ alkyl;

$R^4$ is: H;

$R^5$, $R^6$, $R^7$, $R^8$, $R^9$, $R^{10}$ and $R^{11}$ are, independently, H; unbranched or branched $C_{1-20}$ alkyl or unbranched or branched $C_{1-20}$ alkoxy; $C_{5-9}$ cycloalkyl or $C_{5-9}$ cycloalkoxy; aryl; aryloxy; unbranched or branched $C_{1-20}$ alkylcarbonyl; arylcarbonyl; unbranched or branched $C_{1-20}$ alkoxycarbonyl; aryloxycarbonyl; heteroaryl; carboxyl; cyano; nitro; amido; aminosulfonyl; N-heteroarylsulfonyl; unbranched or branched $C_{1-20}$ alkylsulfonyl; arylsulfonyl; unbranched or branched $C_{1-20}$ alkylsulfinyl; arylsulfinyl; unbranched or branched $C_{1-20}$ alkylthio; arylthio; sulfonamide; halogen; or $N(R^y)(R^z)$, wherein $R^y$ and $R^z$ are independently selected from H and $C_{1-20}$ alkyl; or aryl or aryloxy, respectively substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

17. The method of claim 16, wherein in formula 4 or 5 the neutral ligand L is $P(R^x)_3$, wherein $R^x$ is independently branched or unbranched $C_{1-20}$ alkyl or $C_{1-20}$ alkoxy, $C_{5-9}$ cycloalkyl, or aryl; or RCN, wherein R is branched or unbranched $C_{1-20}$ alkyl, $C_{5-9}$ cycloalkyl, or aryl; or a carbene containing the moiety of formula 6

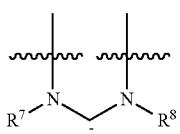

6 wherein $R^7$ and $R^8$ as defined in formula 6 are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen.

18. The method of claim 16, wherein L in formula 4 or 5 is a carbene of one of formulas 6a, 6b, 6c or 6d:

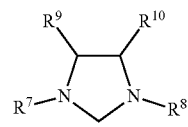

6a

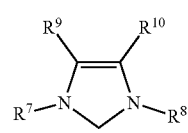

6n

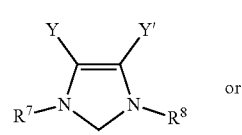

6c or

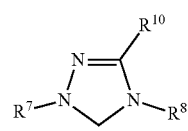

6d wherein $R^9$ and $R^{10}$ are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$ alkoxy or halogen; or $R^9$ and $R^{10}$ together with the carbon atoms to which they are attached are combined to form a carbocyclic 3 to 8 membered ring;

Y and Y' are halogen.

19. The method of claim 16, wherein $R^1$ is $C_{1-6}$ alkyl, optionally substituted with one or more of halogen; or phenyl, optionally substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

20. The method of claim 16, wherein $R^2$ is H.

21. The method of claim 16, wherein $NR^2$—$C(O)$—$R^1$ is in para-position with respect to O.

22. The method of claim 16, wherein $R^3$ is methyl or isopropyl.

23. The method of claim 16, wherein $R^5$ is H.

24. The method of claim 16, wherein $R^6$, $R^7$, $R^8$, and $R^9$ in formula 4 are independently selected from H and halogen.

25. The method of claim 16, wherein $R^{10}$ and $R^{11}$ as defined in formula 5 are independently selected from halogen and cyano.

26. The method of claim 16, wherein L is of formula 6a or 6b, and $R^7$ and $R^8$ as defined in formula 6a and 6b are mesityl, or 2,6-diisopropylphenyl; or
wherein L is of formula

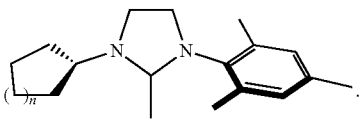

(n = 1 to 8)

27. The method of claim 16, wherein the complex is immobilized on a solid support.

28. The method of claim 15, wherein $R^1$ as defined in claim 15 is nitrogen-containing heterocyclic carbene of structure 7

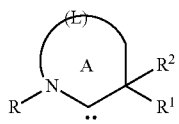

7 wherein the A-ring is a 4-, 5-, 6-, or 7-membered ring; and L in formula 7 is a linking group representing from one to four ring vertices selected from carbon with available valences optionally occupied by hydrogen or optionally substituted by $C_{1-10}$ alkyl and aryl, optionally substituted;
R in formula 7 represents a member selected from $C_{1-10}$ alkyl and aryl, optionally substituted;
$R^1$ and $R^2$ in formula 7 represent independently members selected from $C_{1-10}$ alkyl and aryl, optionally substituted.

29. The method of claim 28, wherein the nitrogen-containing carbene is of formula 7a or 7b:

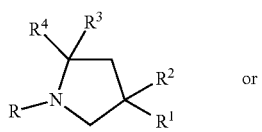

7a or

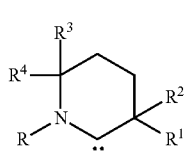

7b wherein R, $R^1$, $R^2$, $R^3$ and $R^4$ in formulae 7a and 7b independently represent a member selected from $C_{1-10}$ alkyl and aryl, optionally substituted.

30. The method of claim 1, wherein the complex is selected from one of the following structures:

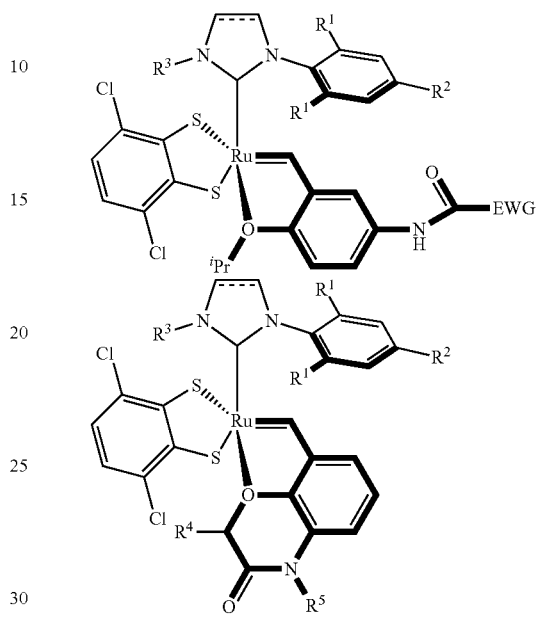

wherein $R^1$ = Me, $^i$Pr. $R^2$ = Me, H. $R^3$ = Ar, Cycloalkyl. $R^4$ = Alkyl. $R^5$ = H, C(O)EWG, and EWG is an electron-withdrawing group.

31. The method of claim 1, wherein more than 50% or 60% or 70% or 80% of the olefin formed in the metathesis reaction according to step (X) or (Y) is a Z-olefin, provided said internal olefin is a Z-olefin; or
wherein the olefin formed in the metathesis reaction according to step (X) is generated predominantly as E-olefin, provided said internal olefin is an E-olefin; or
wherein the olefin formed in the metathesis reaction according to step (Y) is generated predominantly as E-olefin, provided said internal olefin is an E-olefin, and the ring-closing metathesis reaction allows the formation of an E-olefin depending on the ring size.

32. A method of reducing activity loss of a Ru carbene complex comprising a [Ru=C]-moiety when using said complex in a metathesis reaction in which ethylene is developed, the method comprising step (V):

(V) performing said reaction in the presence of an internal olefin.

33. The method of claim 32, wherein said internal olefin is Z-2-butene or E-2-butene.

* * * * *